United States Patent
Keinan et al.

(10) Patent No.: US 8,962,605 B2
(45) Date of Patent: Feb. 24, 2015

(54) POLYCYCLIC COMPOUNDS, TERMED CALIXURENES, AND USES THEREOF

(75) Inventors: Ehud Keinan, Timrat (IL); Galit Parvari, Omer (IL); Doron Pappo, Ramat-Gan (IL)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 13/390,122

(22) PCT Filed: Aug. 12, 2010

(86) PCT No.: PCT/IL2010/000653
§ 371 (c)(1),
(2), (4) Date: Feb. 13, 2012

(87) PCT Pub. No.: WO2011/018790
PCT Pub. Date: Feb. 17, 2011

(65) Prior Publication Data
US 2012/0142912 A1    Jun. 7, 2012

Related U.S. Application Data

(60) Provisional application No. 61/233,158, filed on Aug. 12, 2009.

(51) Int. Cl.
C07D 487/22 (2006.01)
C07D 233/42 (2006.01)
C07D 233/32 (2006.01)
C07D 403/14 (2006.01)

(52) U.S. Cl.
CPC ......... *C07D 233/42* (2013.01); *C07D 233/32* (2013.01); *C07D 403/14* (2013.01); *C07D 487/22* (2013.01)

USPC .................. 514/183; 540/460; 540/461

(58) Field of Classification Search
None
See application file for complete search history.

(56) References Cited

U.S. PATENT DOCUMENTS

2005/0215783 A1    9/2005    Yang et al.

FOREIGN PATENT DOCUMENTS

DE    102005018191    10/2006

OTHER PUBLICATIONS

Qin. Synlett, 2005, 19, 2987-89.*
International Search Report and the Written Opinion Dated Nov. 17, 2010 From the International Searching Authority Re. Application No. PCT/IL2010/000653.
Dave et al. "Novel Macrocycles Incorporating Cyclic Urea Units", Journal of Organic Chemistry, XP002608224, 60: 6946-6952, 1995.
Dave et al. "Synthesis and Structures of a New Class of Calixarene Analogs Derived From 5-T-Butyltetrahydro-1,3,5-Triazine-2(1H)One", Tetrahedron letters, XP002608226, 33(8): 1021-1024, 1992.

(Continued)

*Primary Examiner* — Noble Jarrell

(57) ABSTRACT

Disclosed is a novel family of macrocyclic compounds, coined calixurenes, which comprises linear and cyclic oligomers composed of alternating moieties of an aromatic unit and a ureatic unit, linked to one another via a bridging moiety. The disclosed calixurenes feature multiple heteroatom-containing groups, and can be designed so as to feature other functionalities, and can thus be used in a variety of applications. Further disclosed are processes of preparing the calixurenes, articles containing same and uses thereof.

10 Claims, 3 Drawing Sheets
(1 of 3 Drawing Sheet(s) Filed in Color)

(56) References Cited

OTHER PUBLICATIONS

Kumar et al. "Heterocalixarenes. 1. Calix[2]Uracil[2]Arene: Synthesis, X-Ray Structure, Conformational Analysis, and Binding Character", Journal of Organic Chemistry, XP002608227, 64(21): 7717-7726, 1999.

Kumar et al. "The First Synthesis of Uracil Based Calix[4]Arene Derivatives", Tetrahedron Letters, XP004061971, 38(20): 3607-3608, 1997.

Leung et al. "Effect of Spacer Geometry on Oxoanion Binding by Bis- and Tetrakis- Thiourea Hosts", Tetrahedron, XP022454903, 64(11): 2530-2536, Jan. 11, 2008.

Pratt et al. "Macrocyclic and Macropolycyclic Compounds Based Upon 1,3-Disubstituted Propans Units", Journal of the Chemical Society Perkin Transactions, XP008128690, I: 13-22, 1988.

Shimizu et al. "Self-Assembly of a Bis-Urea Macrocycle Into a Columnar Nanotube", Chemical Communication, XP002608228, p. 1592-1593, 2001.

Weber et al. "Heterocalixarenes Featuring the Benzimidazol-2-One Subunit. Synthesis and X-Ray Structural Studies of Solvent Inclusions", Journal of the Chemical Society Perkin Transactions, XP008128687, 2: 2359-2366, 1996.

International Preliminary Report on Patentability Dated Feb. 23, 2012 From the International Bureau of WIPO Re. Application No. PCT/IL2010/000653.

Communication Pursuant to Article 94(3) EPC Dated Sep. 3, 2014 From the European Patent Office Re. Application No. 10757637.3.

\* cited by examiner

POLYCYCLIC COMPOUNDS, TERMED CALIXURENES, AND USES THEREOF

RELATED APPLICATIONS

This application is a National Phase of PCT Patent Application No. PCT/IL2010/000653 having International filing date of Aug. 12, 2010, which claims the benefit of priority of U.S. Provisional Patent Application No. 61/233,158 filed on Aug. 12, 2009. The contents of the above applications are all incorporated herein by reference.

FIELD AND BACKGROUND OF THE INVENTION

The present invention, in some embodiments thereof, relates to chemistry and, more particularly, but not exclusively, to a novel family of polycyclic (e.g., macrocyclic) compounds which can serve as host molecules and utilized in a myriad of applications.

Polycyclic compounds are defined as linear or cyclic compounds that exhibit a plurality of cyclic moieties linked to one another either directly or indirectly. Polycyclic compounds can be assembled into various cyclic structures, often referred to in the art as macrocyclic compounds. Some macrocyclic compounds are known to act as host molecules to other, guest species.

Macrocyclic host molecules are employed in a large variety of applications and technologies in the fields of chemistry, biology, food, electronics, printing, etc. Macrocyclic host molecules exhibit specific host-guest reversible binding, governed by their chemical nature.

One of the four main known families of macrocyclic host molecules are calixarenes. Calixarenes are basically comprised of phenols that are linked to one another by a short alkylene bridge. Each calixarene contains a repeating phenolic unit formed into a macrocycle via alkylene, typically methylene, bridges. Calixarenes are the product of condensation of phenols and aldehydes. The phenolic unit can be derived from phenol, resorcinol or pyrogallol, and the aldehyde used can be simply a formaldehyde or a larger aldehyde, depending on the nature of the phenolic unit and the desired properties of the formed calixarene. In heterocalixarenes, the phenolic units are replaced by heterocycles, for instance by furans in calix[n]furanes and by pyridines in calix[n]pyridines.

Calixarenes are sparingly soluble and are high temperature melting crystalline solids.

Calixarene nomenclature incorporates the number of repeating aromatic units in the ring. A calix[4]arene has 4 phenols in the ring and a calix[6]arene has 6. A substituent in the meso position (of the carbon atom in a methylene bridging unit) is added to the name with a prefix C- as in, for example, C-methylcalix[6]arene.

Calixarenes are cup-shaped molecules that can form inclusion complexes with a wide range of guest species. The Calixarene "cups" have a vaselike structure defined by an upper rim, lower rim, and central annulus. In calix[4]arenes the internal volume is around 10 cubic nanometers. The polar and non-polar features of the cavities enable calixarenes to interact with a wide range of guest species, depending on the binding groups substituted at each rim and the number of repeating units in the macrocycle.

An exemplary common calixarene, p-tert-butylcalix[4]arene has the following chemical structure:

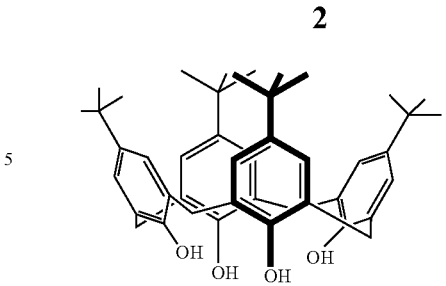

Calixarenes have been used in a wide variety of fields, such as non linear optics, in the field of cation complexation, as sensor devices, in nuclear waste treatment, and as a catalyst in synthetic reactions and liquid crystals. Being efficient sodium ionophores, and capable of exhibiting great selectivity towards other cations, calixarenes are commonly used in chemical sensors, e.g., in commercial applications as sodium selective electrodes for the measurement of sodium levels in blood. Calixarenes also form complexes with cadmium, lead, lanthanides and actinides.

Calixarenes are also applied in enzyme mimetics, ion sensitive electrodes or sensors, selective membranes, non-linear optics and in HPLC stationary phase. In addition, in nanotechnology, calixarenes are used as negative resist for high-resolution electron beam lithography.

Calixarenes are able to accelerate reactions taking place inside the cavity by a combination of local concentration effect and polar stabilization of the transition state.

Currently known sulfur-containing calixarenes include thiacalixarenes, in which there is a thioether bridge between the aromatic units, and, more rarely, thiolcalixarenes (also called mercaptocalixarenes), in which the hydroxyl groups of the phenols are converted to thiols. Exemplary such sulfur-containing calixarenes are described, for example, in H. Kumagai et al., Tetrahedron Lett. 1997, 38, pp 3971-397 and in C. G. Gibbs et al., J. Org. Chem., 1995, 60 (26), pp 8394-8402, as well as in U.S. Pat. No. 6,268,320.

Macrocycles composed of units derived from urea, which have aromatic moieties fused thereto, have been synthesized in the past in low yields. The mechanisms by which these compounds are synthesized (alkaline conditions) preclude use of this synthesis to produce a thiaureatic-containing macrocycle (due to the sulfur's nucleophilicity). Examples of such compounds are described in P. R. Dave et al., J. Org. Chem., 1995, 60 (21), pp 6946-6952 and in E. Weber et al., J. Chem. Soc., Perkin Trans. 2, 1996, pp. 2359-2366.

SUMMARY OF THE INVENTION

The present inventors have designed and successfully prepared and practiced a novel family of polycyclic compounds, which contain urea and/or thiourea, combined with aromatic fragments (optionally phenolic functions), and have coined these compounds $(S)_a$-calix[X,Y]urenes or simply calixurenes.

The unique combination of thiourea and phenolic functional groups in the same molecule allows for modes and strengths of binding, including all scales, from metal atoms to nanoparticles to macroscopic surfaces.

The novel calixurene family is characterized by high modularity, both in terms of the functionalities that can be introduced to the compounds and in terms of the geometries and conformations it can adopt. An inclusion of a thiaureatic unit within the macrocyclic structure features an accessible sulfur, which is more stable than other sulfur-containing groups introduced heretofore to macrocyclic compounds (e.g., thioethers and thiols), and which increases the number of functional groups within the macrocycle cavity.

According to an aspect of some embodiments of the invention there is provided a compound having the general Formula I:

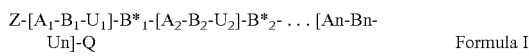

wherein:

n is an integer from 1 to 20;

$A_1, A_2, \ldots, An$ are each independently an aromatic moiety or absent, provided that at least one of $A_1, A_2, \ldots, An$ is the aromatic unit;

$U_1, U_2, \ldots, Un$ are each independently a ureatic moiety or absent, provided that at least one of the $U_1, U_2, \ldots, Un$ is the ureatic moiety;

$B_1, B_2, \ldots, Bn$ and $B^*_1, B^*_2, \ldots, B^*n$ are each independently a bridging moiety or absent;

Z and Q are each independently hydrogen, a functional group or, alternatively, Z and Q form together a bridging moiety.

According to some embodiments of the invention, n is an integer from 2 to 12.

According to some embodiments of the invention, n is an integer from 4 to 20.

According to some embodiments of the invention, n is an integer from 4 to 12.

According to some embodiments of the invention, Z and Q are each independently selected from the group consisting of hydrogen and a functional group, the compound being a linear oligomer.

According to some embodiments of the invention, Z and Q form together a bridging moiety, the compound being a cyclic oligomer.

According to some embodiments of the invention, each of the aromatic moieties independently has a general Formula II:

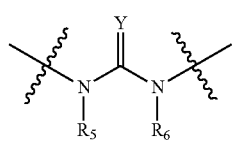

wherein:

$R_1$-$R_4$ are each independently selected from the group consisting of hydrogen, alkyl, alkenyl, alkynyl, cycloalkyl, heteroalicyclic, aryl, heteroaryl a functional group and a heteroatom-containing group.

According to some embodiments of the invention, the heteroatom-containing group is being selected from the group consisting of hydroxy, thiol, alkoxy, thioalkoxy, aryloxy, thioaryloxy, amine, amide, thioamide, carboxyl, thiocarboxyl, carbamate, thiocarbamate, sulfone, sulfoxide, sulfonamide, phosphate, phosphonate, phosphine, cyano, azide, guanyl, guanidine, azo, nitro and hydrazine, and an alkyl, alkenyl, alkynyl or cycloalkyl, each substituted by at least one of the forgoing.

According to some embodiments of the invention, $R_1$ is selected from the group consisting of hydrogen, hydroxy and thiol.

According to some embodiments of the invention, at least one of the $R_1$-$R_4$ is selected from the group consisting of hydroxy and thiol.

According to some embodiments of the invention, each of the ureatic moieties has the general Formula III:

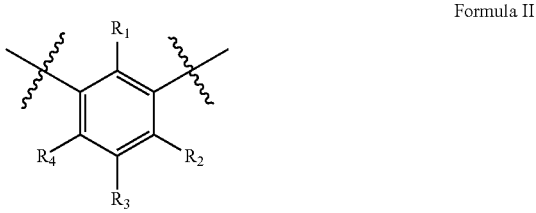

wherein:

Y is selected from the group consisting of O, S and $NR_7$, whereas $R_7$ is hydrogen or alkyl; and $R_5$ and $R_6$ are each independently selected from the group consisting of hydrogen, alkyl, cycloalkyl, heteroalicyclic, heteroaryl and aryl, or, alternatively, $R_5$ and $R_6$ form together a substituted or unsubstituted, 4-, 5-, 6- or 7-membered ring.

According to some embodiments of the invention, Y is selected from the group consisting of O and S.

According to some embodiments of the invention, each of the aromatic moieties is linked to an ureatic moiety or to an aromatic moiety via at least one bridging moiety and each of the ureatic moieties is linked to an ureatic moiety or an aromatic moiety via at least one bridging moiety.

According to some embodiments of the invention, each of the bridging moieties is independently selected from the group consisting of a substituted or unsubstituted alkylene, optionally interrupted by a heteroatom, O, S and $NR_8$, whereas $R_8$ is hydrogen, alkyl, aryl, or cycloalkyl.

According to some embodiments of the invention, each of the bridging moieties is independently a substituted or unsubstituted alkylene.

According to some embodiments of the invention, the alkylene is methylene.

According to some embodiments of the invention, the compound has the general formula:

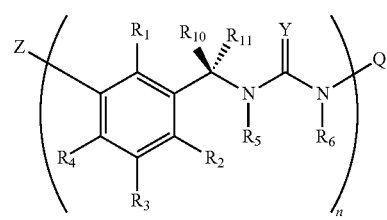

wherein $R_{10}$ and $R_{11}$ are each independently selected from the group consisting of hydrogen, alkyl, cycloalkyl, aryl, halo, hydroxy, thiol, alkoxy, thioalkoxy, aryloxy, thioaryloxy, amine, amide, thioamide, carboxyl, thiocarboxyl, carbamate, thiocarbamate, sulfone, sulfoxide, sulfonamide, phosphate, phosphonate, phosphine, cyano, azide, guanyl, guanidine, azo, nitro and hydrazine.

According to some embodiments of the invention, the compound has the general formula:

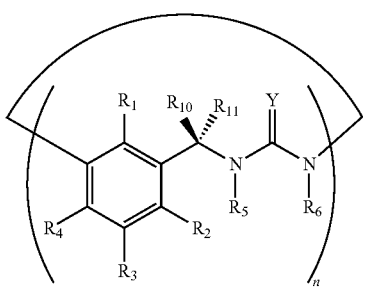

According to an aspect of some embodiments of the invention there is provided a process of preparing the compound disclosed herein, the process comprising reacting at least one aromatic unit and at least one ureatic unit, in the presence of an agent for forming the bridging unit, thereby obtaining the compound.

According to an aspect of some embodiments of the invention there is provided a process of preparing the cyclic compound as disclosed herein, the process comprising:

reacting at least one aromatic unit and at least one ureatic unit, in the presence of an agent for forming the bridging unit, to thereby obtain a linear oligomer having n−1 [A-B-U]-B* units and an aromatic moiety or a ureatic moiety linked thereto; and reacting the linear oligomer having n−1 units with an aromatic moiety or a ureatic moiety, in the presence of an agent for forming the bridging moiety, thereby obtaining the cyclic oligomer.

According to some embodiments of the invention, the agent for forming the bridging unit is selected from the group consisting of an aldehyde, a ketone, an acetal, and a linear or cyclic polyoxymethylene.

According to an aspect of some embodiments of the invention there is provided a host-guest binding pair comprising a cyclic compound as disclosed herein and a guest molecule associated therewithin.

According to an aspect of some embodiments of the invention there is provided an article comprising the compound or the complex described herein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
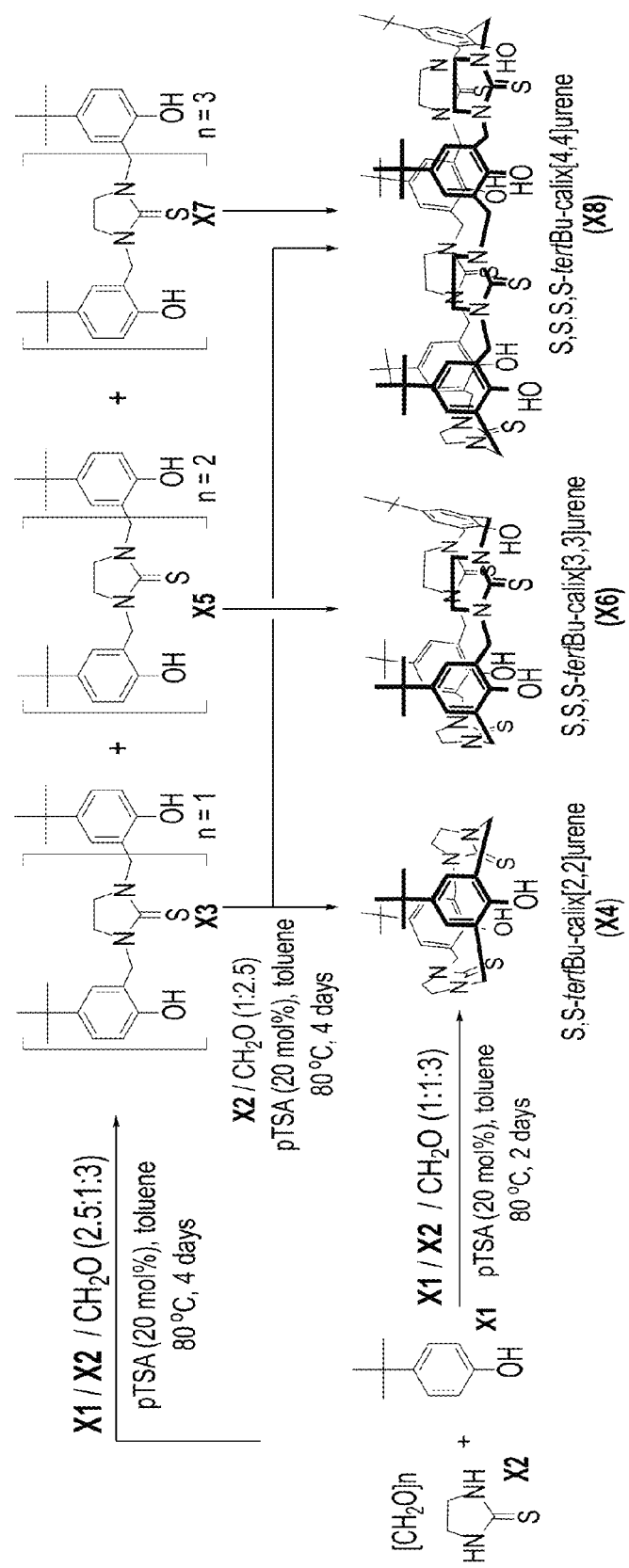
Figure 2:
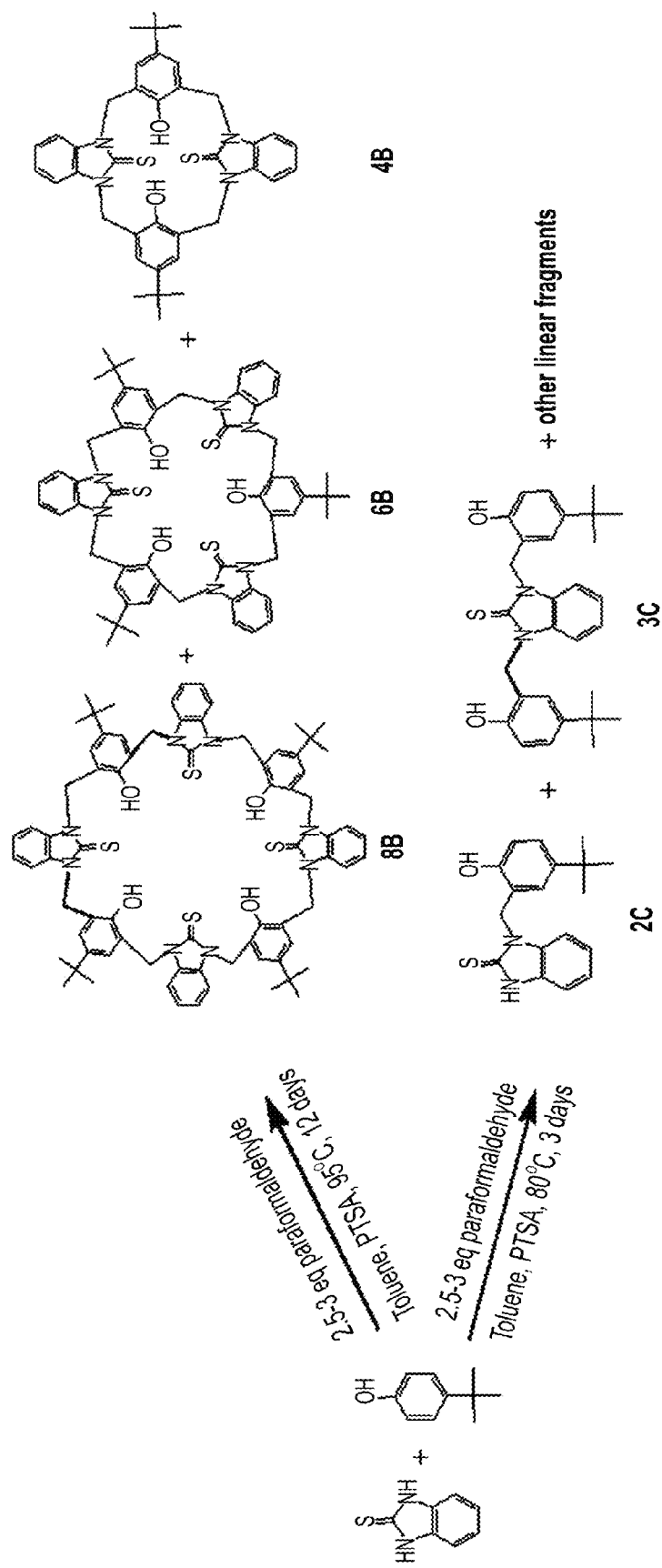
Figure 3:
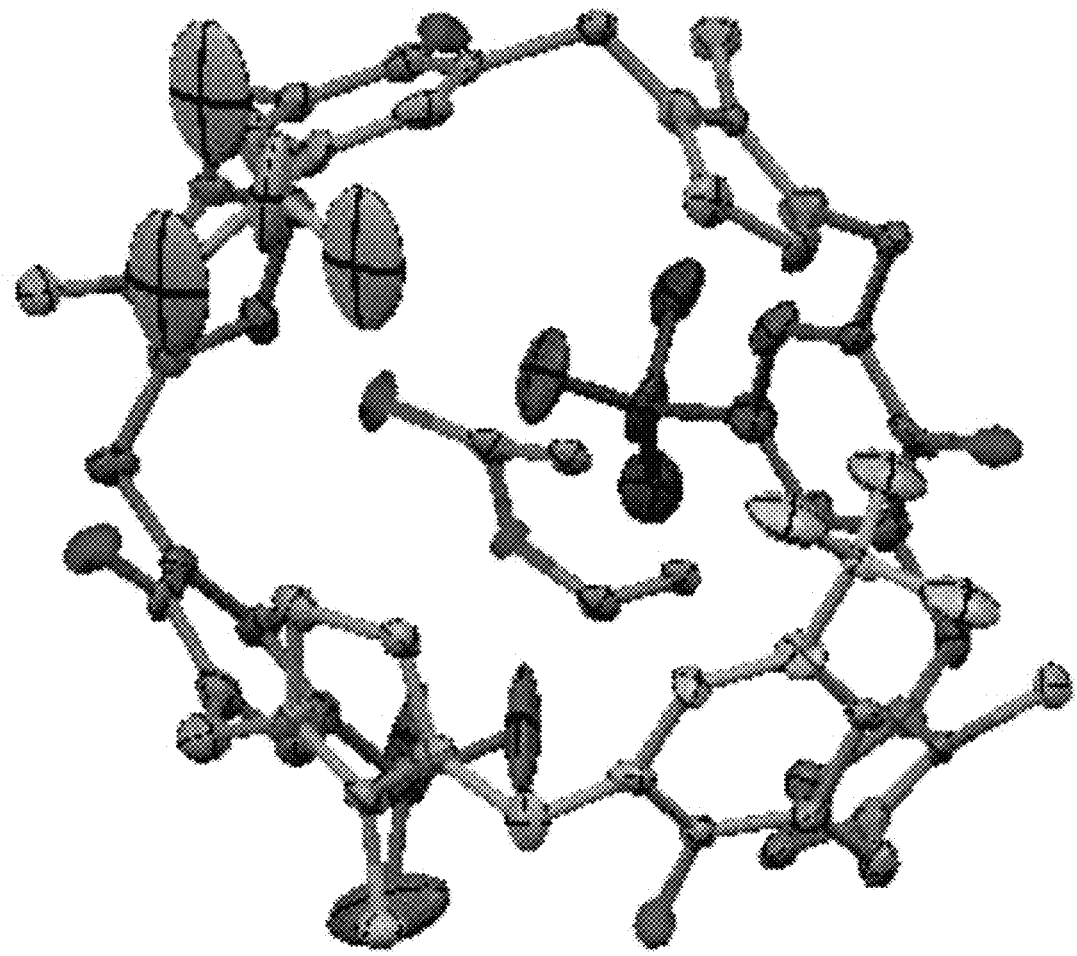

FIG. 1 presents a schematic illustration of exemplary synthetic pathways for preparing linear and cyclic calixurenes composed of 2-imidazolidenthione as an ureatic moiety, para-tertbutylphenol as an aromatic moiety and formaldehyde as an agent for forming the bridging moiety;

FIG. 2 presents a schematic illustration of a synthetic pathway for preparing exemplary linear and cyclic calixurenes composed of 1,3-dihydro-2H-benzimidazole-2-thione as an ureatic moiety, para-tertbutylphenol as an aromatic moiety and formaldehyde as an agent for forming the bridging moiety, according to some embodiments of the invention; and FIG. 3 is an image presenting the crystal structure of S,S,S,S-tert-butylphenolcalixl[4,4]urine hosting an ethyl acetate molecule, as obtained by X-ray diffraction structure determination (Gray denotes carbon, red denotes oxygen, yellow denotes sulfur, blue denotes nitrogens; Hydrogens are omitted for clarity).

DESCRIPTION OF SPECIFIC EMBODIMENTS OF THE INVENTION

The present invention, in some embodiments thereof, relates to chemistry and, more particularly, but not exclusively, to a novel family of polycyclic compounds which can serve as host molecules and utilized in a myriad of applications.

In a search for macrocyclic host molecules with improved performance, the present inventors have designed and successfully prepared and practiced a novel family of polycyclic compounds, which contains units of urea or thiourea (termed herein ureatic units), combined with aromatic units such as phenols or other functionalized aromatic units. These novel polycyclic compounds are coined herein "calixurenes" or, by the more detailed proposed nomenclature $(S)_d$calix[X,Y]urene, wherein S represents the sulfur atoms (if present) featured by the ureatic unit, "d" is an integer denoting the number of sulfur atoms in the calixurene, X denotes the number of aromatic units, and Y denotes the number of ureatic units. In case other heteroatoms are featured by a ureatic unit (e.g., O or N), the "S" is replaced by these atoms. In cases where the aromatic unit is substituted, the substituent is indicated prior to "calix". Linear or cylic prefixes are added at the beginning.

The structure of an exemplary calixurene, termed cyclic-S,S,S,S-tertbutylphenol-Calix[4,4]urene, is as follows:

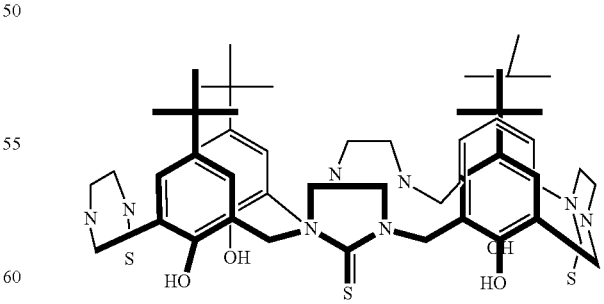

The polycyclic compounds are presented either as linear oligomers, composed of alternating aromatic and ureatic units, or as macrocyclic compounds. These compounds feature a unique combination of functional groups, imparted by the ureatic units and the functionalization of the aromatic unit. This unique combination provides new host-guest chemistry and allows for versatile and controllable modes and strengths of binding.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The Compounds:

According to an aspect of some embodiments of the present invention, there is provided a calixurene compound having the general Formula I:

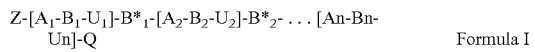

Formula I wherein:

n is an integer from 1 to 20;

$A_1, A_2, \ldots, An$ are each independently an aromatic moiety or absent, provided that at least one of $A_1, A_2, \ldots, An$ is an aromatic moiety;

$U_1, U_2, \ldots, Un$ are each independently a ureatic moiety or absent, provided that at least one of said $U_1, U_2, \ldots, Un$ is an ureatic moiety;

$B_1, B_2, \ldots, Bn$ and $B^*_1, B^*_2, \ldots, B^*n$ are each independently a bridging moiety or absent;

Z and Q are each independently hydrogen, a functional group or, alternatively, Z and Q form together a bridging moiety.

Accordingly, the compounds disclosed herein are oligomeric compounds, comprising two or more alternating units of an aromatic moiety and a ureatic moiety. Thus, a basic unit in these compounds is an aromatic unit covalently linked to a ureatic moiety, as these terms are defined herein. Optionally, the aromatic moiety and the ureatic moiety are linked to one another via a bridging moiety, as defined hereinbelow.

An oligomer unit, as this term is used in the context of Formula I herein, refers to a [A-B-U]-B*- unit, as denoted hereinabove. In each unit, one or more of A, B, U and B* can be absent, such that a unit can comprise A, A-B, A-U, U-B*, A-B-U, B-U or A-B-U-B*.

Thus, the oligomer can comprise, for example, consecutive units of a basic unit, as described hereinabove, or, two or more consecutive aromatic moieties linked to one another, then to one or more consecutive ureatic moieties linked to one another, then to one or more consecutive aromatic moieties, and so forth.

In some embodiments, each oligomer unit in the compound is an [A-B-U]-B* unit, where none of A, B, U and B* is absent.

The $A_1, A_2, \ldots, An$ aromatic moieties can be the same or different.

The $U_1, U_2, \ldots, Un$ ureatic units can also be the same or different.

The $B_1, B_2, \ldots, Bn$ and $B^*_1, B^*_2, \ldots, B^*n$ can also be the same or different.

The variable "n" in general Formula I represents the number of oligomeric units, as described herein, in the compound. In some embodiments, the compound comprises from 1 to 20 oligomeric units, as described herein. However, longer oligomers, with n greater than 20, are also contemplated.

In some embodiments, the number of oligomeric units n ranges from 2 to 12.

In some embodiments, the number of oligomeric units n ranges from 4 to 20.

In some embodiments, the number of oligomeric units n ranges from 4 to 12.

It is to be noted that the number of oligomeric units and the number of each of the ureatic moiety and the aromatic moiety can be the same or different. Thus, for example, in embodiments where each oligomer unit in the compound is an [A-B-U]-B* unit, where none of A, B, U and B* is absent, the number of ureatic moieties is "n", the number of aromatic moieties is "n" and the number of bridging moieties is "2n". In other embodiments, where different oligomer units are used, the number of aromatic moieties, ureatic moieties and bridging moieties varies accordingly.

An aromatic moiety in the compound can be linked to another aromatic moiety or to a ureatic moiety directly or via a bridging moiety. Similarly, a ureatic moiety can be linked to another ureatic moiety or to an aromatic moiety directly or via a bridging moiety.

In some embodiments, each of the aromatic moieties is linked to an ureatic moiety or to an aromatic moiety via at least one bridging moiety and each of the ureatic moieties is linked to an ureatic moiety or an aromatic moiety via at least one bridging moiety.

The presence of a bridging moiety is desired both in terms of facilitating the synthesis of the oligomer and in terms of forming a spacer between the aromatic and/or ureatic moieties. Such a spacer facilitates the formation of macrocyclic compounds, as described herein, and further enables to control the properties of the formed macrocyclic compounds. Such a spacer also enables the independent rotation of the units, which may result in versatile conformations of the structure.

The phrase "bridging moiety", as used herein, describes a bi-radical moiety that is covalently linked to two moieties in the oligomer.

Exemplary bridging moieties that are suitable for use in the context of the present embodiments include, but are not limited to, a substituted or unsubstituted alkylene, optionally interrupted by a heteroatom, and heteroatoms, such as O, S and $NR_8$, whereas $R_8$ is hydrogen, alkyl, aryl, or cycloalkyl.

In some embodiments, each of the bridging moieties is independently a substituted or unsubstituted alkylene, such as methylene.

In some embodiments, the nature of the bridging moiety is determined by the nature of an agent used in the synthesis of a desired compound, as is discussed in further detail hereinbelow.

Typically, a calixurene as described herein is prepared in the presence of an aldehyde such as formaldehyde, or a formaldehyde-generating compound, such as, for example, a polyoxymethylene (e.g., trioxane). Other aldehydes, as well as ketones and acetals, are also contemplated.

The resulting bridging moiety is typically an alkylene, while the alkylene's length, composition and nature of substituents is defined by the reacting agent that forms the bridging moiety (e.g., the reacting aldehyde).

In some embodiments, the nature of the bridging moiety is determined by modifying post-oligomerization the formed bridging moiety. Thus, for example, an alkylene chain formed from an aldehyde can be substituted post oligomerization, as further discussed hereinafter.

As used herein, the phrase "alkylene" refers to a hydrocarbon chain, typically of 1-20 carbon atoms in its backbone chain, preferably of 1-10 carbon atoms, preferably of 1-6 carbon atoms, preferably of 1-4 carbon atoms and more preferably of 1 or 2 carbon atoms. The hydrocarbon chain is therefore composed of methylene units, whereby each methylene can independently be substituted or unsubstituted, and whereby each substituted methylene can be substituted differently.

An alkylene can be represented as —(CRaRb)$_f$—, wherein Ra and Rb are each independently hydrogen, alkyl, cycloalkyl, aryl, halo, hydroxy, thiol, alkoxy, thioalkoxy, aryloxy, thioaryloxy, amine, amide, thioamide, carboxyl, thiocarboxyl, carbamate, thiocarbamate, sulfone, sulfoxide, sulfonamide, phosphate, phosphonate, phosphine, cyano, azide, guanyl, guanidine, azo, nitro and hydrazine, as these terms are defined herein. Each (CRaRb) unit in the chain can be the same or different.

The hydrocarbon chain, when composed of 2 or more methylenes, can be interrupted by one or more heteroatoms, such as, for example, O, S, and/or an amine (e.g., —NR$_8$—), as defined herein. Other heteroatoms (e.g., PR$_8$, Si(R$_8$)$_2$, BR$_8$, Si(OR$_8$)$_2$, P(OR$_8$), and the like, are also contemplated.

As noted hereinabove, in some embodiments, the bridging moiety can be a heteroatom per se, as described herein.

In some embodiments, each of the bridging moieties is independently a substituted or unsubstituted alkylene, such as methylene.

A substituted methylene can have different substituents and thus can impart chirality to the calixurene. Either one or all bridging moieties can feature such chirality.

The calixurenes described herein can be either in a form of a linear oligomer composed of the herein described oligomeric units, or, can be in a form of a macrocyclic molecule.

In some embodiments, Z and Q are each independently selected from the group consisting of hydrogen and a functional group, such that the compound is a linear oligomer.

The phrase "functional group" in the context of the present embodiments, describes any chemical group other than hydrogen, as well as any chemical or biological moiety, which imparts to the oligomer certain functionality.

The functionality can be, for example, in terms of a reactive group that is capable of forming a bond with an additional moiety or substance. Such reactive groups can act, for example, as leaving groups in a nucleophilic-addition reaction, or as nucleophilic group in nucleophilic substitutions, or as groups that participate in addition reactions (e.g., click reaction), or as groups that interact with metals, metal salts, metal ions, surfaces, nanoparticles and the like. Exemplary such groups include, but are not limited to, alkenyl, alkynyl, halo, hydroxy, thiol, alkoxy, thioalkoxy, aryloxy, thioaryloxy, amine, amide, thioamide, carboxyl, thiocarboxyl, carbamate, thiocarbamate, sulfone, sulfoxide, sulfonamide, phosphate, phosphonate, phosphine, cyano, azide, guanyl, guanidine, azo, nitro and hydrazine.

The functionality can further be in terms of a chemical group that imparts hydrophilicity or hydrophobicity to the oligomer. Exemplary such groups include, but are not limited to, hydroxy, carboxyl, phosphate, sulfoxide and the like, for hydrophilicity; and aryls, long alkylene chains (e.g., of 4-30 carbon atoms) and fatty acid moieties, for hydrophobicity.

The functionality can further be in terms of chemical group that imparts other characteristic to the compound. For example, the chemical group can be a positively or negatively charged group, at neutral pH, or can be chiral group.

The functionality can further be in terms of a substance (e.g., a chemical substance, a biological substance, a pharmaceutical, a labeling moiety, a radiolabeled atom or group, a surface, a nanoparticle, as the like), attached to the oligomer.

Z and Q can be the same or different, and can be any of the functional groups described herein.

In some embodiments, Z and Q form together a bridging moiety, such that the compound is a cyclic oligomer.

The bridging moiety represented by —Z-Q-, can be any of the bridging moieties described herein, and can be the same as one or more of B$_1$-Bn and B*$_1$-B*n, or a different bridging moiety.

In some embodiments, the bridging moiety represented by —Z-Q- is a substituted or substituted alkylene, such as methylene.

In some embodiments, all of the bridging moieties, namely, the —Z-Q- bridging moiety in a cyclic compound, and each of B$_1$-Bn and B*$_1$-B*n are the same.

In some embodiments, each of these bridging moieties is a substituted or unsubstituted methylene.

In some embodiments, all of the bridging moieties, namely, the —Z-Q- bridging moiety in a cyclic compound, and each of B$_1$-Bn and B*$_1$-B*n, except one bridging group are the same, whereby one bridging moiety is different (e.g., is a chiral moiety, or is comprising a functional moiety as described herein). Similarly, two or three bridging moieties can be different from the other identical moieties As used herein, an "aromatic moiety", which is also referred to herein interchangeably as "aromatic unit", describes a bi-radical aryl or heteroaryl, as defined herein, optionally substituted by one or more substituents.

In some embodiments, the aromatic unit comprises one or more heteroatom-containing group.

The phrase "heteroatom-containing group", as used herein, encompasses a heteroatom per se and any group that includes one or more heteroatoms.

By "heteroatom" it is meant any atom other than carbon and hydrogen. Exemplary heteroatoms include, but are not limited to, O, S, N and P, yet, other heteratoms such as, for example, halogen, Si and B, are also contemplated.

When the heteroatom-containing group is a heteroatom per se, the heteroatom forms a part of the aromatic unit, in a form of a heteroaryl.

Exemplary heteroatom-containing groups include, but are not limited to, hydroxy, thiol, alkoxy, thioalkoxy, aryloxy, thioaryloxy, heteroalicyclic, amine, amide, thioamide, carboxyl, thiocarboxyl, carbamate, thiocarbamate, sulfone, sulfoxide, sulfonamide, phosphate, phosphonate, phosphine, cyano, azide, guanyl, guanidine, azo, nitro and hydrazine, and an alkyl, alkenyl, alkynyl, aryl or cycloalkyl, each substituted by at least one of the forgoing.

In some embodiments, the heteroatom is O, S and/or N. In some embodiments, the heteroatom is O or S.

The presence of a heteroatom-containing group as a substituent of the aromatic unit affects the host-guest chemistry of the compound and the applications thereof.

The location of a heteroatom-containing group on the aromatic moiety can further determine the properties of the resulting compound. Thus, for example, a heteroatom-containing group in the upper rim of a macrocyclic compound affects its host-guest chemistry.

In some embodiments, one or more of the aromatic moieties is a substituted or unsubstituted aryl.

In some embodiments, each of the aromatic moieties is a substituted or unsubstituted aryl.

Aromatic moieties which are substituted or unsubstituted aryls can be collectively represented by general Formula II:

Formula II

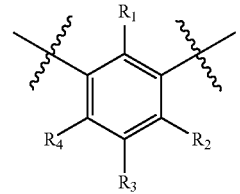

wherein:
the dashed line represents the part of the aryl that constitutes the aromatic moiety within the oligomer or macrocyclic compound; and $R_1$-$R_4$ are each independently selected from the group consisting of hydrogen, alkyl, alkenyl, alkynyl, cycloalkyl, heteroalicyclic, aryl, heteroaryl and a heteroatom-containing group, as defined herein.

In some embodiments, one or more of $R_1$-$R_4$ is a functional group, as defined herein.

In some embodiments, one or more of $R_1$-$R_4$ is a heteroatom-containing group, as defined herein.

In some embodiments, one or more of $R_1$-$R_4$ is hydroxy or thiol.

In some embodiments, one or more of $R_1$-$R_4$ is hydroxy.

In some embodiments, $R_1$ is a heteroatom-containing group.

In some embodiments, $R_1$ is hydroxy or thiol. In some embodiments, $R_1$ is hydroxy, such that the aromatic moiety is derived from a phenol.

In some embodiments, one or both of $R_2$ and $R_4$ is a heteroatom-containing group.

In some embodiments, one or both of $R_2$ and $R_4$ is hydroxy or thiol.

In some embodiments, both of $R_2$ and $R_4$ is hydroxy, such that the aromatic moiety is derived from resorcinol.

In some embodiments, one or more of $R_1$-$R_4$ is hydroxy or thiol.

It is to be noted that aromatic moieties that are linked to other units in the oligomeric structure are also contemplated. Thus, the aromatic moiety can be such that is linked to other moieties at positions meta and/or para to $R_1$ in the above Formula II. The nature of the substituents at other positions can be the same or different.

As used herein, the phrase "ureatic moiety", which is also referred to herein interchangeably as "ureatic unit", describes a moiety derived from urea or thiourea.

The ureatic moieties can be collectively represented by the general Formula III:

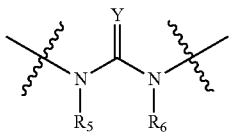

Formula III wherein:

Y is selected from the group consisting of O, S and $NR_7$, whereas $R_7$ is hydrogen or alkyl; and $R_5$ and $R_6$ are each independently selected from the group consisting of hydrogen, alkyl, cycloalkyl and aryl, or, alternatively, $R_5$ and $R_6$ form together a substituted or unsubstituted, 4-, 5-, 6- or 7-membered ring.

In some embodiments, one or more of $R_5$ and $R_6$ is a functional moiety or group, as described herein.

In some embodiments, Y is O, such that the ureatic moiety is derived from urea.

In some embodiments, Y is S, such that ureatic moiety is derived from thiourea. Ureatic moieties derived from thiourea impart to the compound various advantageous traits, as further discussed herein.

Accordingly, in some embodiments, at least one of the ureatic moieties in the described compounds is derived from thiourea, such that Y in Formula III is S.

In some embodiments, each of the ureatic moieties in the described compounds is derived from thiourea.

Optionally, one or more of the ureatic moieties in the described compounds is derived from urea, such that Y in Formula III is O.

In some embodiments, each of the ureatic moieties in the described compounds is derived from urea.

In some embodiments, some of the ureatic moieties in the described compounds are derived from thiourea, and the other ureatic moieties are derived from urea.

Each of the ureatic moieties can be substituted or unsubstituted, as indicated for $R_5$ and $R_6$ in Formula III.

In some embodiments, one or both of $R_5$ and $R_6$ comprise a chiral group, so as to impart chirality to the compound.

In embodiments where $R_5$ and $R_6$ form together a ring, the ring can be a substituted or unsubstituted cycloalkyl, aryl, heteroalicyclic or heteroaryl. In some embodiments, the ring can be further substituted by substituents that form together a ring, which is fused to the ring formed by $R_5$ and $R_6$. The fused ring can be a substituted or unsubstituted cycloalkyl, aryl, heteroalicyclic or heteroaryl. The ring formed by $R_5$ and $R_6$ and/or the ring fused thereto can be chiral.

In some embodiments, each of the oligomeric units [A-B-U] described herein includes an aryl as the aromatic unit, and a methylene as a bridging moiety. Such oligomeric units can be the same or different and can be collectively represented by the following general formula:

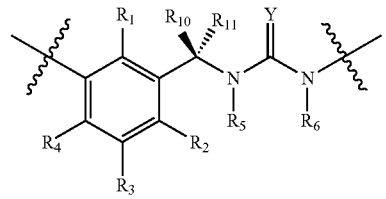

wherein the dashed lines indicate the part of the structure that constitutes that [A-B-U] oligomeric unit, and wherein $R_{10}$ and $R_{11}$ are each independently selected from the group consisting of hydrogen, alkyl, cycloalkyl, aryl, halo, hydroxy, thiol, alkoxy, thioalkoxy, aryloxy, thioaryloxy, amine, amide, thioamide, carboxyl, thiocarboxyl, carbamate, thiocarbamate, sulfone, sulfoxide, sulfonamide, phosphate, phosphonate, phosphine, cyano, azide, guanyl, guanidine, azo, nitro and hydrazine, as defined herein.

Compounds composed of repeating such units are collectively represented by the general formula:

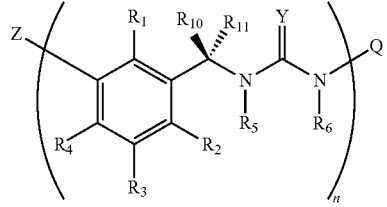

Macrocyclic compounds composed of repeating such units are collectively represented by the general formula:

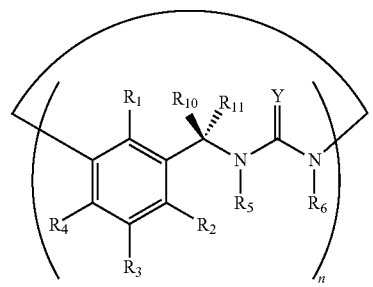

It is to be noted that, as indicated hereinabove, each of the compounds described herein is characterized by the functionality imparted by the inclusion of one or more ureatic units, and can be further exhibit functionality imparted by the presence of heteroatoms in one or more of the aromatic moieties.

Additional functionalities can be imparted by the presence of one or more functional moieties, as described herein, at the end groups Z and/or Q, as one or more substituents on a bridging moiety, as one or more substituents on an aromatic moiety and/or as one or more substituents on a ureatic moiety.

The Syntheses:

According to as aspect of some embodiments of the invention, there is provided a process of preparing the calixurene compounds described herein. The process, according to these embodiments, is generally effected by reacting one or more types of selected aromatic units and one or more types of selected ureatic units, in the presence of an agent for forming the bridging unit.

As used herein, the phrase "an agent for forming the bridging unit" generally describes an agent that can react, generally via a condensation reaction (e.g., nucleophilic addition reaction and/or electrophilic aromatic substitution) with both the aromatic unit and the ureatic unit.

In some embodiments, such an agent is characterized as possessing two leaving groups or one doubly-bonded leaving group. In some embodiments, when the desired bridging moiety is an alkylene, it can have, for example, the following structure: $L_1$-(CRaRb)f-$L_2$, wherein $L_1$ and $L_2$ are the leaving groups. In some embodiments, when the desired bridging moiety is a methylene, it can have, for example, the following structures: $L_1$-(CRaRb)-$L_2$ or (CRaRb)f=L.

Thus, an exemplary agent for forming a methylene bridging moiety can be represented as (CRaRb)d=L, wherein L is a leaving group and Ra and Rb are as described herein for $R_{10}$ and $R_{11}$. Such an agent can be an aldehyde or a ketone. An exemplary leaving group is an oxo group (=O), which generates under the reaction conditions (an acidic environment) two hydroxy leaving groups.

Optionally, an exemplary agent for forming a methylene bridging moiety is represented as $L_1$-(CRaRb)-$L_2$, wherein $L_1$ and $L_2$ are each independently a leaving group and Ra and Rb are as described herein for $R_{10}$ and $R_{11}$. An exemplary leaving group is an alkoxy or thioalkoxy, such that agent is an acetal.

Other suitable leaving groups include, but are not limited to, halo, alkoxy, aryloxy, amine, hydroxy, azide, nitro, cyano, thiocyanate, O-carboxylate, thiol and sulfonate.

Accordingly, in some embodiments, an agent for forming a bridging moiety is an aldehyde or a compound that releases an aldehyde under the reaction conditions. The latter can be, for example, a polyoxymethylene, such as paraformaldehyde and trioxane.

A "polyoxymethylene" encompasses compounds having the formula:

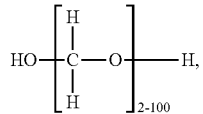

including cyclic forms thereof, and substituted forms thereof (where the carbon is substituted by $R_{10}$ and $R_{11}$ as described herein).

The nature of the agent for forming the bridging moiety can be determined based on the desired features of the bridging moiety.

Using the procedure described hereinabove, linear and/or cyclic compounds can be obtained by controlling the reaction time and conditions.

Cyclic compounds, however, can be obtained via alternative procedures.

One such alternative process is generally described and exemplified as general procedure B in the Examples section that follows.

In some embodiments, another process of preparing a cyclic compound as described herein, is generally effected by reacting one or more types of aromatic units and one or more types of ureatic units, in the presence of an agent for forming said bridging unit, as described herein, to thereby obtain a linear oligomer having n−1 [A-B-U]-B* units and one [A] unit or [U] unit linked thereto; and reacting said linear oligomer having n−1 units with an aromatic unit or a ureatic unit, in the presence of an agent for forming said bridging moiety, thereby obtaining the cyclic oligomer.

In some embodiments, the linear oligomer is selected such that it comprises n aromatic units, and is reacted with an ureatic unit.

In general, the conditions for performing any of the above-described processes include an organic solvent such a toluene, and a presence of an acid, in catalytic, half-stochiometric, or stoichiometric amounts.

The reaction can be performed at room temperature, or, alternatively, while heating, typically to a temperature of up to 100° C.

An exemplary synthetic scheme, for linear and cyclic calixurenes prepared from para-tertbutylphenol (X1) as an aromatic moiety, 2-imidazolethione (X2) as an ureatic moiety and paraformaldehyde as an agent for forming a methylene bridging moiety is presented in FIG. 1. As shown in FIG. 1, linear polymers (X3, X5 and X7), composed of 3, 5, and 7, respectively, aromatic and ureatic units, as well as cyclic polymers (X4, X6 and X8) composed of 4, 6, and 8, respectively, aromatic and ureatic units altogether, can be readily obtained using various synthetic pathways.

Additional details of processes for preparing the disclosed compounds are provided in the Examples section that follows.

In general, the processes of preparing calixurenes are performed at relatively mild conditions, and thus can be readily scaled-up for industrial production.

As used hereinthrouhgout, the term "hydroxy" describes an —OH group.

The term "thiol" describes a —SH group.

The term "alkyl" describes a saturated aliphatic hydrocarbon including straight chain and branched chain groups. Preferably, the alkyl group has 1 to 30 carbon atoms. Whenever a numerical range; e.g., "1-30", is stated herein, it means that the group, in this case the alkyl group, may contain 1 carbon atom, 2 carbon atoms, 3 carbon atoms, etc., up to and including 30 carbon atoms. In some embodiments the alkyl group has 1-20 carbon atoms. In some embodiments, the alkyl group has 1-10 carbon atoms. In some embodiments, the alkyl group has 1-4 carbon atoms. Exemplary alkyl groups include, but are not limited to methyl, ethyl, propyl, butyl, pentyl, hexyl, heptyl, octyl, nonyl, decyl, undecyl, dodecyl, tridecyl, tetradecyl, pentadecyl, heptadecyl, octadecyl and nonadecyl. The alkyl can be substituted or unsubstituted.

The term "alkenyl" describes an alkyl group, as defined herein, which consists of at least two carbon atoms and at least one carbon-carbon double bond.

The term "alkynyl" describes an alkyl group, as defined herein, which consists of at least two carbon atoms and at least one carbon-carbon triple bond.

The term "cycloalkyl" describes an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted.

The term "aryl" describes an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted.

When an alkyl, alkenyl, alkynyl, aryl, cycloalkyl, heteroalicyclic and heteroaryl is substituted, the substituent group can be, for example, alkyl, cycloalkyl, aryl, heteroaryl, heteroalicyclic, hydroxy, alkoxy, aryloxy, thiohydroxy, thioalkoxy, thioaryloxy, cyano, carbonyl, thiocarbonyl, O-carbamyl, N-carbamyl, O-thiocarbamyl, N-thiocarbamyl, C-amido, N-amido, C-carboxy, O-carboxy, nitro, sulfonamido, trihalomethanesulfonamido, silyl, guanyl, guanidino, ureido, amino or NRaRb, as defined herein, wherein Ra and Rb are each independently hydrogen, alkyl, cycloalkyl, aryl, carbonyl, sulfonyl, trihalomethysulfonyl and, when combined, a five- or six-member heteroalicyclic ring.

The term "alkoxy" describes both an —O-alkyl and an —O-cycloalkyl group, as defined herein.

The term "aryloxy" describes both an —O-aryl and an —O-heteroaryl group, as defined herein.

The term "thioalkoxy" describes both an —S-alkyl group, and an —S-cycloalkyl group, as defined herein.

The term "thioaryloxy" refers to both an —S-aryl and an —S-heteroaryl group, as defined herein The term "cyano" describes a —C≡N group.

The term "carbonyl" describes a —C(=O)—R' group, where R' is hydrogen, alkyl, cycloalkyl, aryl, heteroaryl (bonded through a ring carbon) or heteroalicyclic (bonded through a ring carbon) as defined herein.

The term "ketone" describes a R'—C(=O)—R" group, where R' is as defined herein and R" is as defined for R', independently.

The term "thiocarbonyl" describes a —C(=S)—R' group, where R' is as defined herein.

The term "thioketone" describes a R'—C(=S)—R" group, where R' and R" are as defined herein The term "carbamate" describes an —OC(=O)—NR'R" group, where R' is as defined herein and R" is hydrogen, alkyl, cycloalkyl, aryl, heteroaryl (bonded through a ring carbon) or heteroalicyclic (bonded through a ring carbon) as defined herein, or a R'OC(=O)—NR"— group, where R' and R" are as defined herein.

The term "thiocarbamate" describes an —OC(=S)—NR'R" group, where R' and R" are as defined herein, and an R"OC(=S)NR'— group, where R' and R" are as defined herein.

The term "amide" describes a —C(=O)—NR'R" group, where R' and R" are as defined herein, and an R'C(=O)—NR" group, where R' and R" are as defined herein.

The term "carboxylate" describes a —C(=O)—O—R' groups, where R' is as defined herein, and an R'C(=O)—O— group, where R' is as defined herein.

The term "nitro" group describes an —NO₂ group.

The term "sulfonamide", encompasses both an "S-sulfonamido" and "N-sulfonamido" wherein an "S-sulfonamido" group describes a —S(=O)₂—NR'R" group, with R' is as defined herein and R" is as defined for R'. An "N-sulfonamido" group describes an R'S(=O)₂—NR" group, where R' and R" are as defined herein.

The term "trihalomethanesulfonamido" group refers to an T₃CS(=O)₂NR'— group, wherein T is a halo group as defined herein and R' is as defined herein.

The term "guanidino" group describes an —R'NC(=N)—NR"R'" group, where R', R" and R'" is hydrogen, alkyl, cycloalkyl, aryl, heteroaryl (bonded through a ring carbon) or heteroalicyclic (bonded through a ring carbon) as defined herein.

The term "guanyl" group describes an R'R"NC(=N)— group, where R' and R" are as defined herein.

The term "silyl" describes a —SiR'R"R'", where R', R" and R'" are as defined herein.

The term "amino" group describes an —NR'R" group, where R' and R" are as described herein.

The term "sulfone" group describes an —S(=O)₂—R' group, where R' is as defined herein.

The term "sulfoxide" describes as S(O)R' group, with R' as defined herein.

The term "halogen" or "halo" describes fluoro, chloro, bromo or iodo atom.

The Applications:

Based on the modularity of the disclosed calixurenes, the enhanced functionally thereof, and the controllable configuration thereof, these compounds possess traits considered as unique and surpassing those of the previously known macrocycles.

The calixurene compounds disclosed herein can be designed to include numerous heteroatoms which are unprecedently exposed and can form novel geometries, thus creating extraordinary ligands. For example, a thiophillic metal ion can be bound by more than a single sulfur atom (part of the thiocarbonyl group in S-calixurene) without the "entopic cost" of bringing several such binders together. There are currently no known macrocycles that include as many sulfur atoms in the same macrocycle. Also, calixurenes offer "tuning ability" to the type of factor they serve as ligands for. This tuning is expressed not only in the initial size of the Calixurene used, but also in its flexibility to alter the angles and distances of the dentates to optimal values for the strongest possible binding interaction.

The calixurenes disclosed herein further offer a novel variety of internal cavities. The characteristics of these cavities— hydrophobicity, electron densities, sizes, shapes and more—can all be altered by altering the moieties composing the compounds, as described herein. Therefore, a wide variety of atoms and molecules, neutral or charged, may form host-guest association with various members of the calixurene family. Furthermore, as has been demonstrated by X-Ray structures (of S,S,S-tertbutylphenol-Calix[4,4]urene) (see, FIG. 3), Calixurenes—especially of the larger sizes, have innate flexibility and can "fold" around guests which are relatively smaller than their "original" internal volume. This in-situ modification of the host's inner cavity is reminiscent of some proteins.

Thus, according to as aspect of some embodiments of the invention there is provided a host-guest complex which comprises a cyclic calixurene, as described herein having a suitable guest associated therewith.

The calixurenes disclosed or the complexes disclosed herein can be used in a myriad of applications, including, but not limited to, drug delivery, chelation therapy, protein binding and tagging, specific ion binding and delivery, chemical analysis, surface chemistry, modification of surface properties and functionalization, nanotechnology, nanoparticles, nanoelectronics, catalysis, asymmetric synthesis, membrane modifications, ion channels, functional polymers, adhesives, to list a few.

The calixurenes disclosed herein can thus be utilized in fields such as Chemistry, Physics, Nanotechnology, Medicine and pharmaceuticals, Food and cosmetics, Agriculture and environmental protection, Construction and preservation, Electronic devices and their fabrication tools, Media storage and dissemination, New materials (such as plastics, artificial membranes and tissues, etc.), Transportation, entertainment and sports (if the new materials created incorporating Calixurenes, or are affected by processes achieved with Calixurenes are used in these fields), and Energy.

The following discussed some of the applications of the disclosed calixurenes. It is noted that the modularity of the calixurene enables to control the functionality of the compound, so as to suit it for a desired application, as is further detailed hereinafter.

Chemical catalysis: As in the case of cucurbiturils, calixarenes, and other macrocylic host molecules, the calixurene compounds described herein can function as ligands for metal catalysts and/or for influencing the stereoselectivity of a reaction occurring within or in proximity to the calixurene's cavity.

In some embodiments, the calixurenes disclosed herein are used for complexing metal ions or metal catalysts. Such calixurenes are designed as featuring functional groups and/or electronic properties suitable for such a complexation. Examples include, but are not limited to, functionalities exhibited by the carbonyl and/or thiocarbonyl groups of the ureatic moiety in the calixurene and/or functionalities exhibited by the substituents on the bridging moiety or on other moieties in the calixurene.

In some embodiments, the calixurenes are used in chemical reactions so as to catalyze reactions within its hydrophobic cavity. Hydrophobicity of the calixurene cavity can be manipulated, for example, by the nature of heteroatoms and substituents on the different moieties (aromatic, ureatic, and bridging).

In some embodiments, calixurenes feature a chiral moiety, as exemplified herein above, are used for influencing the stereoselectivity of chemical synthesis.

An example for a possible catalyzed reaction is for two reactants, one featuring a functional azide group and another reactant featuring a functional alkyne, to undergo a "click" addition reaction within the Calixurene cavity.

Additional reactions can be performed using calixurenes to which one or both reactants are bound or coordinated.

The performance of a calixurene in any of the above-describes chemical syntheses is determined by performing the reaction is the presence and absence of calixurene, and determining the role of the calixurene in increasing the reaction rate, the reaction yield and/or the reaction selectivity.

Biological catalysis and enzyme mimetics As previously described for calixarenes, calixurenes can be designed so as to function as an enzyme mimetic for catalyzing biological reactions. To this effect, calixurenes are designed so as to coordinate or bind one or more of the biological molecules, and to facilitate the reaction by inducing an environment stabilizing the reaction's transition state. The substituents on the calixarenes could provide this particular member of the Calixurene family with high water solubility, and yet its cavity could be maintained as hydrophobic, thus enabling hydrophobic moieties of the reactants to enter or coordinate as guests. Furthermore, as many biological reactions, mediated by enzymes, require the presence of a metal ion (as occurs in metalloenzymes), the Calixurene could be tailored to coordinate to the required metal ion as well as orienting the reactants correctly in relation to this metal ion.

Nanoparticle coating: Nanoparticles having modified surface are becoming a common practice in various applications. By coating nanoparticles with the calixurenes disclosed herein, versatile properties can be imparted to the nanoparticles, as desired. For example, hydrophobic nanoparticles can be formed and thus utilized in applications that require a hydrophobic medium.

In some embodiments, "multiple" calixurenes, formed by attaching two or more calixurenes to one another, are used. These create "tubes" whose segments are made of Calixurenes. Such calixurenes can be formed from a calixurene having one type of reactive groups on any of the aromatic units and the ureatic units and a calixurene having another type of reactive groups on any of the aromatic units and the ureatic units, such that the two types of reactive groups react so as to form bonds or coordination. The "multi" calixurene typically has an inverted structure, such that the heteroatoms point outward. Such calixurenes, as well as other suitably functionalized calixurenes, can be used as "nanoparticle glue", for binding nanoparticles. Such calixurenes can further be designed to reversibly release the bound nanoparticles in a desired medium, by, for example, forming degradable bonds in the "multiple" calixurene.

In some cases, where the adhesion to the nanoparticle is double or multi-faceted, nano clusters could be formed in which the distance of separation between individual particles is set and predicted.

Nanoparticles coating by calixurenes can be determined by a variety of methods including spectroscopy, adhesion to resins, DLS (dynamic light scattering) and more.

Surface modification: Surfaces which feature a certain set of traits (such as hydrophilicity) can be modified by attaching thereto the calixurenes disclosed herein. The calixurenes typically attach to the surface via the heteroatoms of the ureatic units. If the binding to the surface is done via, for example, the "lower rim", then the nature of the "upper rim" thus attributes to the modified surface the desired traits (e.g., hydrophobicity), and can be controlled as desired by introducing the appropriate functionalities to any of the aromatic unit, the ureatic unit and/or the bridging unit, as described hereinabove. Surface modification can be effected such that a minimal number (as low as one) of calixurene layers are attached to the surface, thus avoiding further interference with the surface functionality (e.g., thickness).

Surface modification can further be performed by utilizing the host function of the calixurenes, such that the modified surface can be utilized for selectively capturing suitable guest molecules. Surface modification can further be performed by utilizing functional groups of the calixurenes for binding other moieties.

Surfaces modification by calixurenes can be determined by a variety of surface analysis techniques, including water contact angle measurements, XPS (X-ray photoelectron spectroscopy), surface plasmon resonance (SPR), electron microscopy, etc.

Sensors: Macrocycles of various types serve as sensors for a very wide variety of analytes (gases, organic and inorganic atoms and molecules in liquid phases, etc.). Often, the analyte binds either to the hydrophobic cavity/moiety, or to the heteroatoms. To the macrocycle which serves as sensor a group is connected which by itself serves as a reporting unit (such as a fluorescent group, thus, upon analyte detection a shift in wavelength and/or intensity occurs) or as a linker to an external sensing unit (such as a connection via a conductive portion to field effect transistors, which show a shift in current-voltage parameters). Calixurenes can serve as both kinds of sensors (through linkers and/or functional groups upon one or more of their various functionalization sites). Calixurenes are expected to excel in cases where the analyte interacts with the hydrophobic moiety and the heteroatoms are bound to surfaces—these latter serve as part of the detection unit (such as in a field effect transistor), thus circumventing the need for additional linkers (between the host and the detector) which often reduce the sensor's potential sensitivity. Selectivity for analytes can be tuned according to the Calixurene's size, composition, and substituents.

Immobile/mobile phases for purification and separation: Due to expected superior metal binding and new guests for host-guest binding, calixurenes which bind a desired target (light, transition and heavy metals, organic and inorganic molecules, charged or neutral, etc.) so as to form a stable complex, could serve for capturing such a target from within a mixture (gas, liquid, or solid). This capturing can be of controlled temporality, based on a chemical/physical treatment to release the target, or for a long duration. This enables, for example, using calixurenes for separating a desired material from another material or from a mixture by solid phase separation (chromatography), or for the purification of industrial wastes from heavy metals, so that after the addition/contact of the solution with Calixurenes the waste emerges without or with a highly reduced concentration of the heavy-metal pollutant.

Controlled release: Based on the binding capabilities of calixurenes to a desired substance, and the ability to control the reversibility of the binding, a system can be designed such that the values of the binding constants and diffusion rates in a required medium are controlled. For example, a system can be designed such that a steady concentration of the substance is maintained in the medium. Such a system can be designed, for example, for releasing odorous materials (such as perfume) from a calixurene-including matrix into gas or liquid environments, or systems such as biological creams/gels, for releasing a desired substance to the skin or mucosal organs.

The duration of the release can also be flexibly set, and conditioned with other factors, so as to control the onset of a substance's release. For example, a system can be designed to release an insecticide only during night time in a planted field, or so as to release nutrients into soil only when the environment is wet/dry enough. These "conditions" would be expressed via direct affects on host-guest interactions, or by attaching proper functional units to the calixurene.

Drug delivery: Drugs which have specific targets in the body often fail to reach these at the optimal levels due to transportation problems to the target and/or decomposition in the physiological environment. Calixurenes could serve for both protecting the drug from certain types of degradation in the body (e.g., due to low gastric pH or enzymatic reactions), and for releasing a drug at a desired bodily target. The latter can be achieved by designing a modified calixurene that undergoes partial or full decomposition by an enzyme that is overexpressed at the desired bodily site, so as to allow diffusion of the drug out of the modified calixurene at this site. The calixurene can further include a targeting moiety attached thereto, aimed at targeting the modified calixurene to the desired bodily site (via a proper receptor, for example), where the guest drug is released by diffusion. For monitoring purposes, such calixurenes can further include a labeling moiety (e.g., fluorescent tags, radioactive elements, etc.).

Preservation: Given a stable complex with the molecule to be preserved, a calixurene "wrapping" may afford it increased stability under conditions which could cause its degradation. For example, an organic molecule folded into the cavity of a calixurene could be less inclined for degradation by UV light since UV-breakable bonds can re-form in the folded fixation rather than enabling the decomposed molecule to react further with its environment. Molecules which are sensitive to oxygen (e.g., metals and metal ions) which are complexed to a calixurene could be exposed to oxygen with a lowered sensitivity.

Protein markers and immobilization: Proteins are a subject of intense research and industrial interest. Tagging proteins specifically and with high efficiency and durability of the tag and its connection to the protein is therefore of high importance. Calixurenes could serve as this type of linker—for example, binding to a protein via a functionalized group on one side (one rim), and binding a nanoparticle or surface on their other side (the heteroatom-containing, other rim). Furthermore, additional functional groups could be added which have a "reporter" functionality—thus "reporting" when the connection between a protein and a nano-particle surface was achieved (for example, through a change in fluorescence). This lowers the requirement for intense surface analysis by electronic microscopes, for example, to verify that the immobilization has occurred.

Selective membranes: The internal cavity of Calixurenes can serve not only as a "den" for guests but also as a channel. The traits of the cavity can be set so that the guests capable of passing through this channel are selected, thus creating a channel only for these species. Calixurenes can be incorporated, via hydrophobic/hydrophilic interactions alone, or via functional groups, to membranes, therefore creating a selective membrane.

The calixurenes disclosed herein can further be utilized similarly to calixarenes, in any of the applications known to utilize the latter. These include, for example, Polymers (including dendrimers) and polymer additives, glues and resins, resists for microfabrication (photolithography, for example), charge control agents (in tuners, printing), OLEDs and transistors, photovoltaics.

All of the above-described applications can be combined so as to create various articles, such as, for example, sensors made of modified surfaces, nanoparticles-based catalysts, etc.

Accordingly, according to an aspect of some embodiments of the invention there is provided an article which comprises any of the calixurene compounds described herein.

Exemplary such articles include, but are not limited to, a surface having said compound applied thereon, a nanoparticle coated by said compound, a drug-delivery system comprising a bioactive agent attached to or incorporated within said compound, a chemical reagent, a biological reagent, a separation system, an edible substance, a light-sensitive substance attached to or incorporated within said compound, an oxygen-sensitive substance attached to or incorporated within said compound, a cosmetic product, an agricultural product, and a pharmaceutical product.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Chemical Syntheses

Materials and Experimental Methods

All chemicals and solvents were purchased from SigmaAldrich and were used without further purification.

NMR studies were performed using Bruker Advance 300 and Bruker Advance 500 instruments. TMS was used as a standard, sample solvents are detailed below for each measurement.

High Resolution Mass Spectrometry (HRMS) studies were performed using a Waters LCT Premier Micromass instrument, in an ESI:negative mode. This instrument was also used for regular (non high-resolution) MS measurements.

Syntheses of Linear Oligomers

General Procedure I:

The calixurenes described herein are generally prepared by reacting a selected aromatic unit (e.g., for example a substituted or unsubstituted phenol and/or resorcinol) and a selected ureatic unit (e.g., a substituted or unsubstituted urea and/or thiourea), in the presence of a selected aldehyde, used for forming a bridging unit, and a catalytic amount of an acid. The concentration of the ureatic unit typically ranges from 0.01 M to 0.1 M. According to the desired alternating oligomer, the ratio between the aromatic unit and ureatic unit is pre-determined. An agent for forming the bridging unit, for example paraformaldehyde or trioxane, is added (in an excess of 2 mol equivalents or more with respect to the ureatic unit).

The selected agent for forming the bridging unit is added to a mixture of the aromatic unit, the ureatic unit, a solvent (such as toluene), and a catalytic amount (e.g., 10-40% mol of the ureatic unit) of an acid (e.g., para-toluenesulfonic acid) is added. The reaction mixture is stirred, optionally while heating to a temperature of up to 100° C. The reactions are typically completed within 1-14 days, as determined by TLC.

Once the reaction is completed, the reaction mixture is cooled to room temperature, and the solvent is evaporated. The residue is optionally thereafter solvated into an appropriate organic solvent (such as dichloromethane or chloroform) and washed with an alkaline aqueous solution. The organic solvent is evaporated, and the crude residue is purified by silica gel column chromatography, using typically a mixture of ethyl acetate and hexane as eluent, yielding from 10% to >90%, of the desired linear oligomer.

The general synthetic pathway is exemplified in Scheme 1 below

Scheme 1

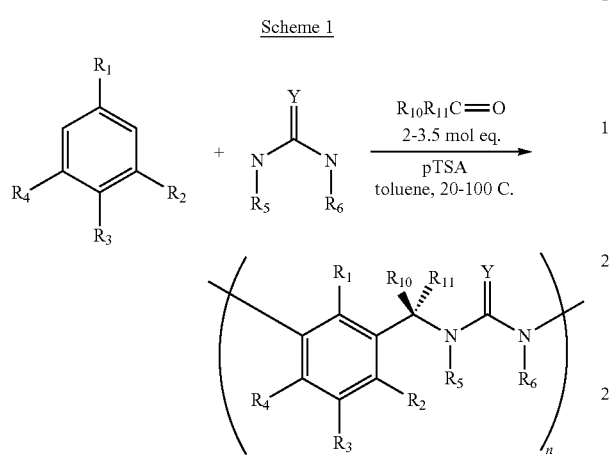

Using the above general procedure the following exemplary linear oligomers were prepared using 2-imidazolidenthione as the ureatic unit, para-tert-butylphenol as the aromatic unit, and paraformaldehyde as the agent for forming the bridging unit, as follows.

Synthesis of 1-benzylimidazolidine-2-thione (Linear S-tertbutylphenol-Calix[1,1]urene, Compound 2)

Compound 2

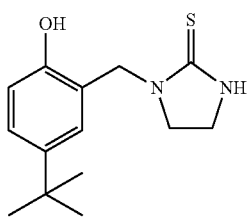

2-Imidazolidenthione (0.2 gram, 1.96 mmol), para-tert-butylphenol (0.6 gram, 3.99 mmol), paraformaldehyde (0.2 gram, 6.67 mmol), and monohydrate para-toluenesulfonic acid (0.11 gram, 0.59 mmol) were heated in toluene (30 ml) at 60° C. for 3 days. The reaction mixture was cooled to room temperature and the toluene was evaporated. The crude residue was purified on a silica gel column (using a mixture of ethyl acetate:hexane from 1:3 up to 3:2, as eluent), thereby affording Compound 2 (0.146 gram, 28% yield). Compound 3 (described below) was obtained as a side product.

$^{zzz1}$H NMR (500 MHz; CDCl$_3$): δ=7.84 (s, OH, 1H), 7.27 (dd, j=5 Hz, j=10 Hz, 1H), 7.07 (d, j=5 Hz, 1H), 6.90 (d, j=10 Hz, 1H), 5.76 (s, NH, 1H), 4.75 (s, 2H), 3.72 (m, 2H), 3.60 (m, 2H), 1.30 (s, 9H) ppm.

$^{13}$C NMR (from HMBC, 125 MHz, CDCl$_3$): δ=182.0, 153.7, 142.7, 128.0, 119.7, 77.5, 48.5, 41.7, 31.7 ppm.

HR-MS: m/z calcd for $C_{14}H_{20}N_2OS$ [M–H]$^-$ 263.1218; found 263.1200.

Synthesis of 1,3-bis(5-tert-butyl-2-hydroxybenzyl) imidazolidine-2-thione (Linear S-tertbutylphenol-Calix[2,1]urene, Compound 3)

Compound 3

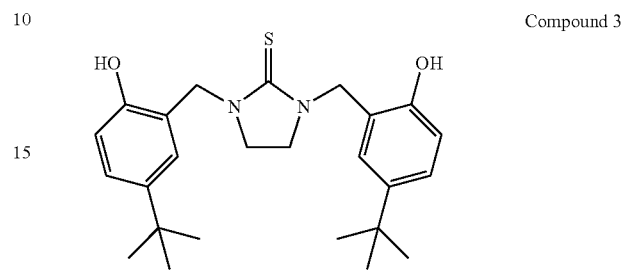

2-Imidazolidenthione (2 grams, 19.6 mmol), para-tert-butylphenol (11.8 grams, 78.6 mmol), paraformaldehyde (1.6 gram, 58.8 mmol) and monohydrate paratoluensulfonic acid (0.75 gram, 3.92 mmol) were heated in toluene (250 ml) at 70° C. for 3.5 days. The reaction mixture was cooled to room temperature and the toluene was evaporated. The crude residue was loaded and separated on a silica gel column (using a mixture of ethyl acetate:hexane 1:3, as eluent), thereby affording Compound 3 (5.27 grams, 63% yield).

$^1$H NMR (300 MHz, CDCl$_3$): δ=7.301 (s, OH, 2H), 7.240 (dd, j=2.7 Hz, j=7.5 Hz, 2H), 6.985 (d, j=2.7 Hz, 2H), 6.832 (d, j=7.5 Hz, 2H), 4.681 (s, 4H), 3.494 (s, 4H), 1.223 (s, 9) ppm.

$^{13}$C NMR (from HMBC, 125 MHz, CDCl$_3$): δ=179.1, 153.1, 142.4, 128.1, 119.3, 117.2, 49.5, 45.7, 34.1 ppm.

HR-MS: m/z calcd for $C_{25}H_{34}N_2O_2S$ [M–H]$^-$ 425.2263; found 425.2271.

Synthesis of 3,3'-(5-tert-butyl-2-hydroxy-1,3-phenylene)bis(methylene)bis(1-(5-tert-butyl-2-hydroxybenzyl)imidazolidine-2-thione) (Linear S,S-tertbutylphenol-Calix[3,2]urene, Compound 5)

Compound 5

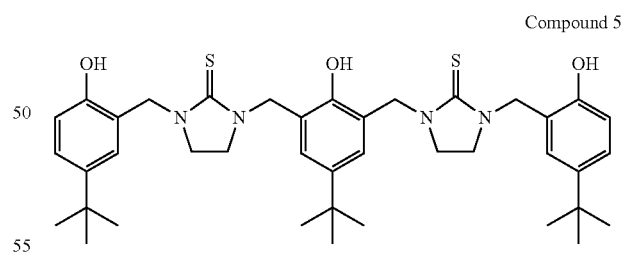

2-Imidazolidenthione (1 gram, 9.8 mmol), para-tert-butylphenol (2.2 grams, 14.8 mmol), paraformaldehyde (1.176 gram, 39.2 mmol) and monohydrate paratoluensulfonic acid (0.621 gram, 3.27 mmol) were heated in toluene (250 ml) at 70° C. for 4 days. The reaction mixture was cooled to room temperature and the toluene was evaporated. The crude residue was dissolved in dichloromethane (30 ml) and the solution was washed with saturated sodium bicarbonate aqueous solution. The organic phase was then evaporated and the residue was separated on a silica gel column (using ethyl acetate:hexane 1:3, as eluent), thereby affording Compound 5

(0.82 gram, 24% yield). Compounds 2 and 3, described hereinabove, were also isolated as by-products.

$^1$H NMR (300 MHz, DMSO-d6): δ=9.309 (s, OH, 2H), 8.515 (s, OH, 1H), 7.213 (d, j=2.1, 2H), 7.156 (s, 2H), 7.090 (dd, j=2.1 Hz, j=8.7 Hz, 2H), 6.738 (d, j=8.7 Hz, 2H), 4.760 (s, 4H), 4.692 (s, 4H), 3.470 (s, 8H), 1.178 (s, 27H) ppm.

$^{13}$C NMR (500 MHz, CDCl$_3$): δ=181.31, 155.14, 153.20, 144.51, 144.22, 130.43, 129.76, 128.83, 123.57, 121.52, 118.69, 50.69, 49.30, 47.89, 47.36, 35.70, 33.32 ppm.

HR-MS: m/z calcd for $C_{40}H_{54}N_4O_3S_2$ [M−H]$^-$ 701.3559; found 701.3589.

Synthesis of 3,3'-(3,3'-(2-thioxoimidazolidine-1,3-diyl)bis(methylene)bis(5-tert-butyl-2-hydroxy-3,1-phenylene)bis(methylene)bis(1-(5-tert-butyl-2-hydroxybenzyl)imidazolidine-2-thione) (Linear S,S,S-tertbutylphenol-Calix[4,3]urene, Compound 7)

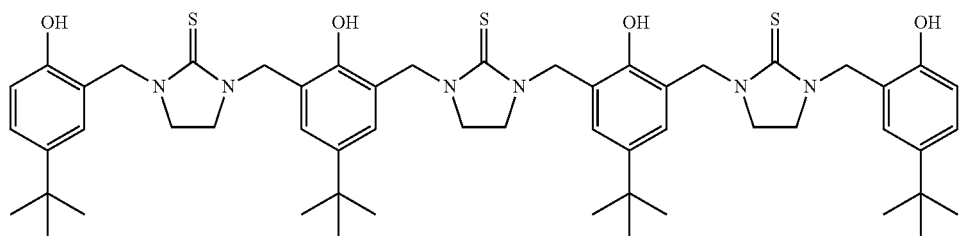

Compound 7

2-Imidazolidenthione (2.5 grams, 24.5 mmol), para-tert-butylphenol (5.5 grams, 36.6 mmol), paraformaldehyde (1.5 gram, 50.0 mmol) and monohydrate paratoluensulfonic acid (1.0 gram, 5.26 mmol) were heated in toluene (250 ml) at 70° C. for 4 days. The reaction mixture was cooled to room temperature and the toluene was evaporated. The crude residue was dissolved in dichloromethane (30 ml) and washed with saturated sodium bicarbonate aqueous solution. The organic phase was separated and evaporated, and the residue was separated on a silica gel column (using ethyl acetate: hexane 1:3, as eluent), thereby affording Compound 7 (0.79 gram, 9.9% yield). Compounds 2, 3 and 5, described hereinabove, were obtained as by-products.

$^1$H NMR (300 MHz, DMSO-d6): δ=9.30 (s, 2H), 8.51 (S, 2H), 7.21 (d, j=3 Hz, 2H), 7.15 (s, 4H), 7.08 (dd, j=3 Hz, j=9 Hz, 2H), 6.73 (d, j=Hz, 2H), 4.76 (s, 8H), 4.69 (s, 4H), 3.47 (s, 12H), 1.18 (s, 36H) ppm.

$^{13}$C NMR (125 MHz, DMSO-d6): δ=180.5, 170.8, 153.7, 152.0, 142.5, 128.5, 127.2, 122.5, 120.1, 117.2, 49.2, 47.9, 47.1, 46.2, 34.1, 31.7 ppm.

HR-MS: m/z calcd for $C_{55}H_{75}N_6O_4S_3$ [M−H]$^-$ 979.5012; found 979.4979.

General Procedure II:

In an alternative procedure, a two-step synthetic pathway is used for preparing linear oligomers, as follows.

First, the selected ureatic unit (e.g., substituted or unsubstituted urea and/or thiourea) is reacted with the agent for forming the bridging unit (for example, an aldehyde such as formaldehyde). This reaction is often fast, occurring within a few hours, and the obtained intermediate, a ureatic unit with bridge-precursors, is filtered out of the solution. The number of bridging-precursors on the ureatic unit is determined and controlled by selecting the concentration ratio between the agent for forming the bridging unit and the ureatic unit.

Second, the ureatic unit with bridge-precursor(s) is reacted with a selected aromatic unit (e.g., a substituted or unsubstituted phenol and/or recorcinol), in the presence of a catalytic amount (e.g., 10-40% mol of the ureatic unit) of an acid (e.g., para-toluenesulfonic acid), in a solvent such as toluene. No additional agent for forming the bridging unit is added at this stage. The concentration of the with bridge-precursor(s) typically ranges from 0.01 M to 0.1 M. According to the desired alternating oligomer, the ratio between the aromatic unit and ureatic unit with bridge-precursor(s) is pre-determined. The reaction mixture is stirred, optionally while heating to a temperature of up to 100° C. The reactions are typically completed within 1-14 days, as monitored by TLC.

Once the reaction is completed, the reaction mixture is cooled to room temperature, and the solvent is evaporated. The residue is optionally thereafter solvated into an appropriate organic solvent (such as dichloromethane or chloroform) and washed with an alkaline aqueous solution. The organic solvent is evaporated, and the crude residue is separated by silica gel column chromatography, using typically a mixture of ethyl acetate and hexane as eluent, yielding from 10% to >90%, of the desired oligomer.

In an exemplary procedure, 1,3-bis(5-tert-butyl-2-hydroxybenzyl)imidazolidine-2-thione (Compound 3), was prepared as follows:

Synthesis of 1,3-bis(hydroxymethyl)imidazolidine-2-thione (Compound 1) (as an example for a thiaureatic unit with two formaldehyde bridge-precursors)

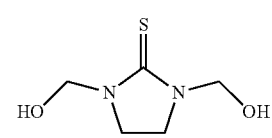

Compound 1

2-Imidazolidenthione (24 grams, 0.235 mol) was added into 2N aqueous HCl (240 ml) and the mixture was heated to 50° C. until all solids dissolved. Thereafter, 34-38% aqueous formaldehyde (50 ml, 0.648 mol) was added and the reaction mixture was heated to 65° C. As the reaction proceeded, the product precipitated as a white solid. After about 30 minutes, the reaction was stopped, cooled to room temperature and the white solid product was filtered out, thereby affording Compound 1 (28.5 grams, 75% yield).

$^1$H NMR (300 MHz, DMSO-d6): δ=5.45 (s, 4H), 4.58 (2H) 3.57 (S, 4H) ppm.

Synthesis of Compound 3 via General Procedure II

Compound 1 (0.2 grams, 1.23 mmol), para-tert-butylphenol (0.6 grams, 4.0 mmol), and monohydrate paratoluensulfonic acid (0.38 gram, 2.0 mmol) were heated in toluene (30 ml) at 60° C. for 3 days. The reaction mixture was cooled to room temperature and the toluene was evaporated. The crude residue was loaded and separated on a silica gel column (using a mixture of ethyl acetate:hexane 1:3, as eluent), thereby affording Compound 3 (0.32 grams, 61% yield).

Syntheses of Cylic Calixurenes

Cyclic calixurenes of various ring sizes are prepared via several synthetic pathways, of which 3 exemplary procedures are as follows:

General Procedure A ("One Pot" Reaction):

A ureatic unit (1 mole equivalent, usually at about 0.01 M), an aromatic unit (1 mole equivalent), and an agent for forming the bridging unit (such as an aldehyde, 2 or more mole equivalents), are reacted in a suitable solvent (for example toluene), in the presence of a catalytic to stoichiometric amount of an acid (e.g., paratoluenesulfonic acid), as described hereinabove for preparing linear oligomers (see, general procedure I).

This synthetic pathway, if enough time and proper conditions are granted, tends to provide a majority of product that appears to be the thermodynamic product for the relevant system. For example, after one week in 60° C. an 8-unit cyclic Calixurene is the main product for the reactants para-tertbutylphenol, 2-imidazolidenthione and paraformaldehyde, with catalytic amounts of para-toluenesulfonic acid (other reactants, such as differently substituted phenols or thiaureas could lead to cyclic products in which another sized-cycle is the preferred, thermodynamic product).

Typically, a thermodynamically favored cyclic calixurene is obtained as the major product while using equimolar amounts of the ureatic and aromatic units, with a surplus of the bridging unit, catalytic to half stoichiometric amount of the acid catalyst, and heating the reaction mixture to the same temperature as required for the synthesis of the corresponding linear oligomers. The time period required for obtaining a thermodynamically favored cyclic calixurene is typically longer than that required for the completion of the shorter, linear Calixurenes. This procedure is exemplified in Scheme 2 below.

Scheme 2

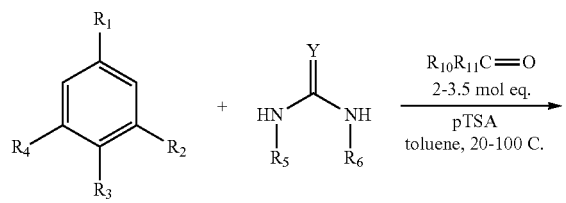

General Procedure B ("Multiple Building Blocks" Reaction):

Stoichiometric amounts of the desired building block(s) (Compound 2, for example) are mixed with 1 mole equivalent or more of an agent for forming the bridging unit (such as an aldehyde), under the same conditions described in general procedure A hereinabove.

This procedure is generally illustrated in Scheme 3 below.

Scheme 3

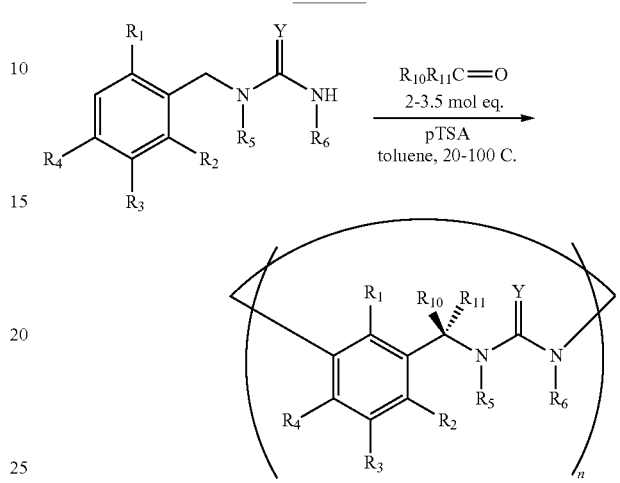

This synthetic pathway typically produces a mixture of cyclic products, differing from one another by ring size (e.g. 4, 6, 8 and 12 unit cyclic products) and/or composition (different sequence of units). The obtained cyclic products can be separated by chromatography (such as HPLC) or by selective complexation with suitably sized guests (such as different metal cations).

General Procedure C ("Ring Minus 1" Reaction):

A linear oligomer (1 mol equivalent) of selected length which corresponds to the number of units in the desired cyclic product, minus 1 unit, is reacted with a desired monomeric unit (1 mol equivalent), to close the ring, in the presence of an excess (e.g., 2 or more mol equivalents) an agent for forming the bridging unit (e.g., trioxane) and a catalytic to stochiometric amount of an acid (e.g., paratoluenesulfonic acid), in a suitable solvent (e.g., toluene). The concentration of the ureatic unit (and correspondingly of other reactants) typically ranges from 0.01M to 0.05M. Reaction duration time usually ranges from 1 to 2 weeks, and is monitored by TLC.

This synthetic pathway is typically characterized by high selectivity towards the desired product, and in some cases is effected in shorter duration time.

This procedure is generally illustrated in Scheme 4 below.

Scheme 4

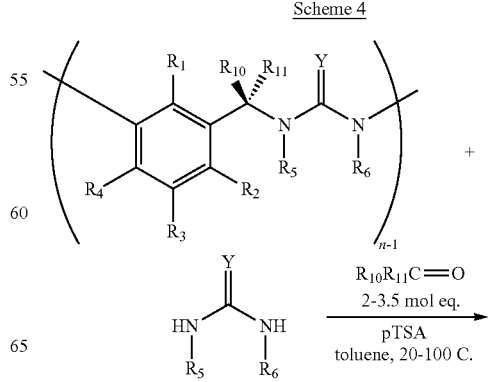

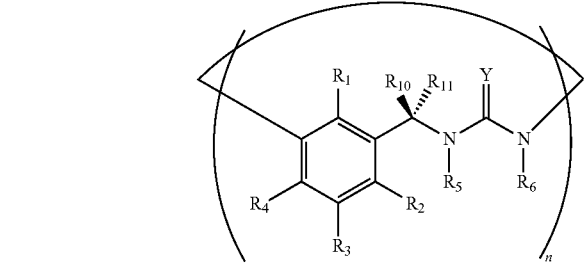

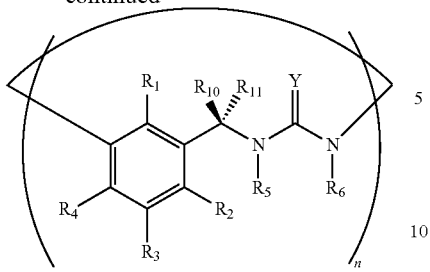

The following describes the preparation of exemplary cyclic calixurenes, deriving from 2-imidazolidenthione, para-tert-butylphenol and paraformaldehyde or trioxane, via the above-described synthetic pathways. The preparation of variously modified cyclic calixurenes is presented hereinbelow.

Synthesis of Cyclic S,S,S-tertbutylphenolcalixl[3,3]urene (Cyclic Compound 6)

Cyclic Compound 6

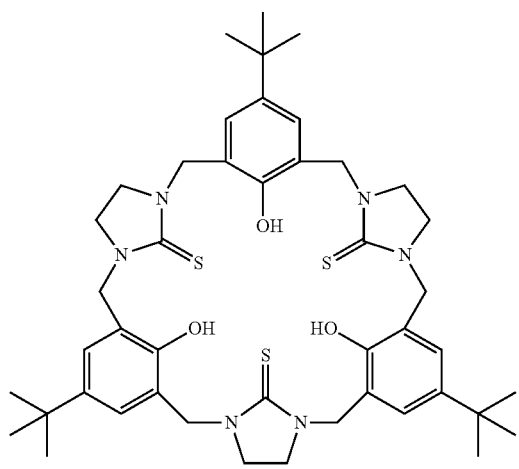

Cyclic compound 6 was prepared using general Procedure C as follows: 3,3'-(5-tert-Butyl-2-hydroxy-1,3-phenylene) bis methylene)bis(1-(5-tert-butyl-2-hydroxybenzyl) imidazolidine-2-thione) (Compound 5, 0.303 gram, 0.43 mmol), paraformaldehyde (0.065 gram, 2.16 mmol), para-toulenesulfonic acid (pTSA, 0.041 gram, 0.22 mmol) and imidazolidine-2-thione (0.044 gram, 0.43 mmol) were mixed in toluene (AR grade, 10 ml), and the reaction mixture was heated to 60° C. for 24 hours. The reaction mixture was thereafter cooled to room temperature and the solvent was removed under reduced pressure. The crude solid product was dissolved in a hot 1M aqueous solution of NaOH (about 60 ml), and the obtained suspension was filtered to remove non-soluble impurities. The filtrate was neutralized to pH=7 by the addition of HCl, resulting in precipitation of the product as an off-white solid. The product was filtered out, washed with water and methanol and dried under vacuum (67% yield).

$^1$H NMR (500 MHz, DMSO-d6): δ=8.503 (br. s, 3H), 7.156 (s, 6H), 4.765 (s, 12H), 3.495 (s, 12H), 1.168 (s, 27H) ppm.

$^{13}$C NMR (151 MGz, DMSO-d6): δ=181.1, 150.4, 141.7, 125.5, 123.0, 46.1, 45.5, 33.5, 31.2 ppm.

HR-MS: m/z calcd for $C_{45}H_{59}N_6O_3S_3$ [M–H]$^-$ 827.3811; found 827.3846.

Synthesis of Cyclic-S,S,S,S-tertbutylphenolcalixl[4,4]urene (Cyclic Compound 8)

Cyclic Compound 8

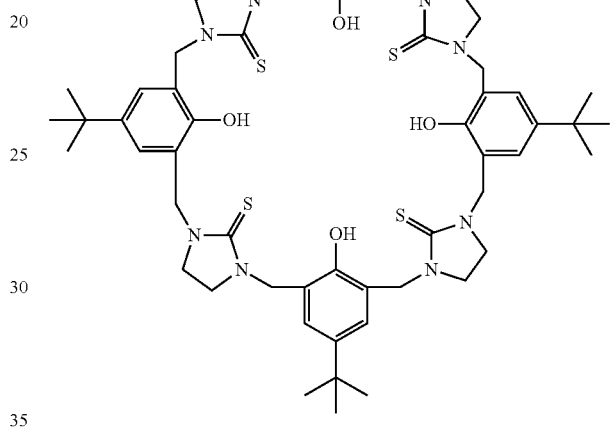

By Procedure A (one-pot reaction): Para-tert-butylphenol (5 grams, 0.033 mol), paraformaldehyde (10 grams, 0.34 mol), pTSA (3.17 grams, 0.017 mol) and imidazolidine-2-thione (10.2 grams 0.1 mol) were mixed in toluene (AR grade, 500 ml). The reaction mixture was heated to 55° C. for 6 days, and then cooled to room temperature. The solvent was removed under reduced pressure, the crude solid product was dissolved in hot 1M aqueous solution of NaOH (about 1 liter), and the obtained suspension was filtered to remove non-soluble impurities. The filtrate was neutralized to pH=7 by the addition of HCl, resulting in precipitation of the product as an off-white solid. The product was filtered out, washed with water and methanol and dried under vacuum (67% yield).

$^1$H NMR (500 MHz, CDCl$_3$): δ=8.260 (br), 7.269 (s, 8H), 4.793 (s, 16H), 3.580 (s, 16H), 1.272 (s, 36H) ppm.

$^{13}$C NMR (125 MHz, CD$_2$Cl$_2$): δ=180.59, 151.51, 142.21, 127.73, 121.96, 47.52, 46.13, 33.71, 31.16 ppm.

HR-MS: m/z calcd for $C_{60}H_{80}N_8O_4S_4$ [M+Na]$^+$ 1127.5083; found 1127.5076.

The crystal structure of the obtained product is presented in FIG. 3.

By Procedure C (ring-1 reaction): 3,3'-(3,3'-(2-thioxoimidazolidine-1,3-diyl)bis(methylene)bis(5-tert-butyl-2-hydroxy-3,1-phenylene)bis(methylene))bis(1-(5-tert-butyl-2-hydroxybenzyl)imidazolidine-2-thione) (Compound 7, 0.239 gram, 0.24 mmol), paraformaldehyde (0.037 gram, 1.22 mmol), pTSA (0.023 gram, 0.12 mmol) and imidazolidin-2-thione (0.0253 gram, 0.24 mmol) were mixed with toluene (AR grade, 10 ml). The reaction mixture was heated to 60° C. for 24 hours, and then cooled to room temperature. The solvent was removed under reduced pressure, the crude solid residue was dissolved in hot 1M aqueous solution of NaOH (about 30 ml), and the obtained suspension was filtered to remove non-soluble impurities. The filtrate was neutralized to pH=7 by the addition of HCl, resulting in precipitation of pure product as an off-white solid. The product was filtered out, washed with water and methanol and dried under vacuum, thereby affording Cyclic Compound 8 (180 mg, 68% yield).

Modified Linear and Cyclic Calixurenes

Using the above-described general procedures, modified linear and cyclic compounds were prepared by functionalizing the aromatic unit, the ureatic unit and/or the bridging unit, as generally described and exemplified in the following.

Modification of the Aromatic Unit

Functionalization of the aromatic unit is performed either pre-oligomerization/cyclization or post-oligomerization/cyclization.

Functionalization of the aromatic ring is performed, for example, for introducing heteroatoms to the substituted aromatic unit, using, for example, starting materials with differently positioned or numbered substituents. Functional groups can be introduced in a number of different positions, so as to impart the obtained calixurene a desired functionality (e.g., for attaching other moieties). Modification can also aim for using materials of higher reactivity in order to increase the rate of synton formation.

In some embodiments, linear oligomers or corresponding cyclic compounds are prepared using the general and exemplary procedures described hereinabove, while replacing the para-tert-butylphenol by variously substituted aromatic species.

The preparation of exemplary modifications of the aromatic unit is presented in the following.

Synthesis of methyl-3-(4-hydroxyphenyl)propionate-substituted Compound 3 (Linear S-4-(methylpropionate)-phenol-Calix[2,1]urene, Compound 3A)

Compound 3A

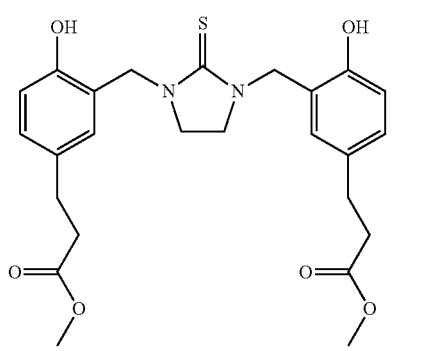

2-Imidazolidenthione (1 gram, 9.8 mmol), methyl-3-(4-hydroxyphenyl)propionate (3 grams, 16.6 mmol), paraformaldehyde (0.7 gram, 23.3 mmol) and monohydrate paratoluensulfonic acid (0.14 gram, 7.4 mmol) were heated in toluene (70 ml) at 70° C. for 6 days. The reaction mixture was cooled to room temperature and the toluene was evaporated. The crude residue was separated on a silica gel column (using ethyl acetate:hexane 1:3, as eluent), thereby affording Compound 4 (1.26 gram, 26.4% yield).

$^1$H NMR (300 MHz, CDCl$_3$): δ=7.04 (dd, j=3.51 Hz, 2H), 6.94 (d, j=2.22 Hz, 2H), 6.84 (d, j=8.25 Hz, 2H), 4.72 (s, 4H), 3.65 (s, 6H), 3.53 (s, 4H), 2.85 (t, j=7.62 Hz, 4H), 2.58 (t, j=7.62 Hz, 4H) ppm.

Synthesis of methyl-3-(4-hydroxyphenyl)propionate-substituted Compound 5 (Linear S,S-4-(methylpropionate)-phenol-Calix[3,2]urene Compound 5A)

Compound 5A

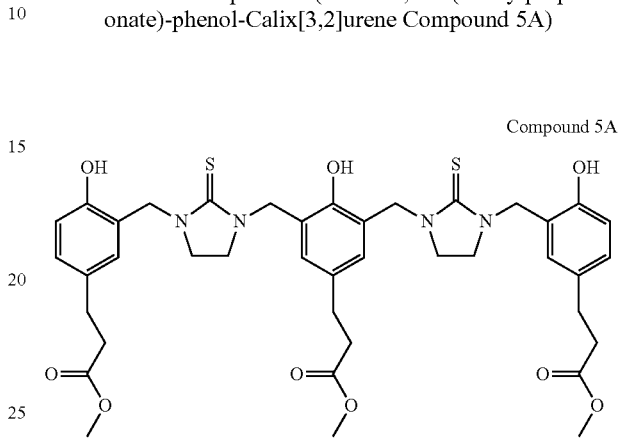

2-Imidazolidenthione (1 gram, 9.8 mmol), methyl-3-(4-hydroxyphenyl)propionate (3 grams, 16.6 mmol), paraformaldehyde (0.7 gram, 23.3 mmol) and monohydrate paratoluensulfonic acid (0.14 gram, 7.4 mmol) were heated in toluene (70 ml) at 70° C. for 6 days. The reaction mixture was cooled to room temperature and the toluene was evaporated. The crude residue was separated on a silica gel column (using ethyl acetate:hexane 1:3 as eluent), thereby affording Compound 6 (0.63 gram, 16.3% yield).

$^1$H NMR (500 Mhz, CDCl$_3$): δ=7.90 (s, 1H), 7.69 (s, broad, 2H), 7.05 (s, 2H), 7.04 (d, j=3.53 Hz, 2H), 6.93 (s, 2H), 6.83 (d, j=8.15 Hz, 2H), 4.75 (s, 4H), 4.73 (s, 4H), 3.66 (s, 9H), 3.55 (m, 8H), 2.85 (m, 6H), 2.59 (m, 6H) ppm.

HR-MS: m/z calcd for $C_{40}H_{48}N_4O_9S_2$ [MH]$^+$ 793.2941; found 793.2936.

Synthesis of phenyl-substituted Compound 3 (Linear S-4-phenyl-phenol-Calix[2,1]urene Compound 3B)

Compound 3B

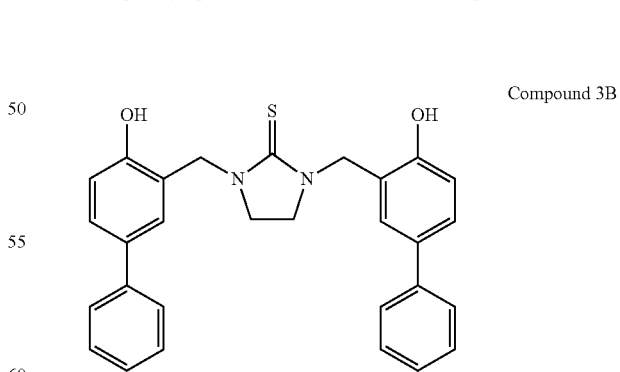

2-Imidazolidenthione (0.2 gram, 1.96 mmol), 4-hydroxybiphenyl (1.0 grams, 5.88 mmol), trioxane (0.18 gram, 1.96 mmol) and monohydrate paratoluensulfonic acid (0.07 gram, 0.39 mmol) were heated in toluene (30 ml) at 55° C. for 5 days. The reaction mixture was cooled to room temperature and the toluene was evaporated. The crude residue was separated on a silica gel column (using ethyl acetate:hexane 1:3 as eluent), thereby affording Compound 3B (0.24 gram, 26% yield).

¹H NMR (300 MHz, CDCl₃): δ=7.51-7.31 (m, 14H), 7.03 (d, j=8.3, 2H) 4.85 (s, 4H), 3.61 (s, 4H) ppm.

¹³C NMR (From HMBC) (500 MHz, CDCl₃): δ=179.5, 155.3, 140.6, 133.1, 129.9, 128.9, 127.3, 126.9, 120.8, 120.4, 118.2, 48.7, 45.8 ppm.

HR-MS: m/z calcd for $C_{29}H_{26}N_2O_2S$ [M+H]⁺ 466.1793; found 466.1765.

Modification of the Bridging Unit

Functionalization of the bridging unit is performed either pre-oligomerization or cyclization (by functionalizing the agent for forming the bridging unit) or post-oligomerization or cyclization (by functionalizing the formed bridging unit).

Functionalization of the bridging unit is performed, for example, for introducing chiral units to the formed structure or can also aim for using materials of higher reactivity in order to increase the rate of synton formation. Functional groups can be introduced in a number of different positions, so as to impart the obtained calixurene a desired functionality (e.g., for attaching other moieties).

In some embodiments, linear oligomers or corresponding cyclic compounds are prepared using the general and exemplary procedures described hereinabove, while replacing the demonstrated paraformaldehyde by a desired aldehyde, ketone, or other agent for forming different bridging groups.

Synthesis of phenyl-bridged Compound 2 (Compound 2A)

An exemplary chiral derivative of Compound 2 was prepared as follows:

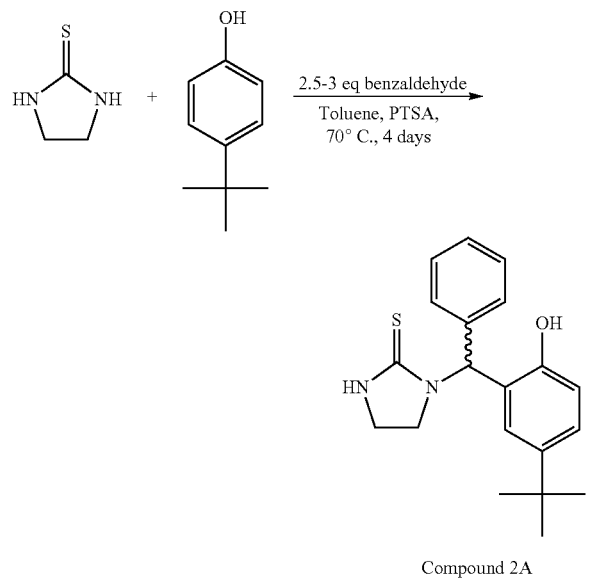

Compound 2A

2-Imidazolidenthione (0.47 gram, 4.6 mmol), para-tertbutylphenol (0.69 grams, 4.6 mmol), benzaldehyde (0.95 mL, 9.2 mmol) and monohydrate paratoluensulfonic acid (0.44 gram, 2.3 mmol) were heated in toluene (50 ml) at 70° C. for 4 days. The reaction mixture was cooled to room temperature and the toluene was evaporated. The crude residue was separated on a silica gel column (using ethyl acetate:hexane 1:3 as eluent), thereby affording Compound 2A (1.56 gram, 33% yield).

¹H NMR (500 Mhz, CDCl₃): δ=7.41 (m, 3H), 7.36 (d, 1H), 7.23 (d, 2H), 6.95 (m, 2H), 5.92 (s, 1H), 4.11 (m, 1H), 3.7 (m, 1H), 3.58 (dt, 1H), 3.31 (q, 1H), 1.19 (s, 9H) ppm.

Modification of the Ureatic Unit

Functionalization of the ureatic unit is performed either pre-oligomerization/cyclization or post-oligomerization/cyclization.

Functionalization of the ureatic unit is performed, for example, for introducing functionalities and/or chiral units to the formed structure or can also aim for using materials of higher reactivity in order to increase the rate of synton formation.

In some embodiments, linear oligomers or corresponding cyclic compounds are prepared using the general and exemplary procedures described hereinabove, while replacing the demonstrated 2-imidazolidenethione by a desired ureatic unit.

Exemplary ureatic units include substituted imidazolidenethione, and substituted and unsubstituted imidazolidinone. The substitutents can be selected so as to impart chirality to the formed structure.

In some embodiments, imidazolidinone is used an the ureatic unit, as exemplified in the following:

Synthesis of 3,3'-(5-tert-butyl-2-hydroxy-1,3-phenylene)bis(methylene)bis(1-(5-tert-butyl-2-hydroxybenzyl)imidazolidin-2-on) (Linear O,O-tertbutylphenol-Calix[3,2]urene Compound 5B Compound 5B

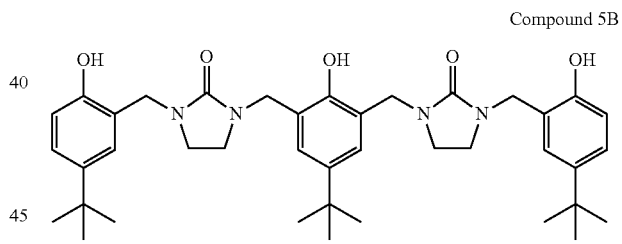

2-Imidazolidinone (1 gram, 11.6 mmol), para-tertbutylphenol (5 grams, 33.3 mmol), paraformaldehyde (1 gram, 33.3 mmol) and monohydrate paratoluensulfonic acid (0.60 gram, 3.16 mmol) were heated in toluene (100 ml) at 70° C. for 1 day. The reaction mixture was cooled to room temperature and the toluene was evaporated. Chloroform (50 ml) was added, and the solution was washed with a saturated aqueous sodium bicarbonate solution. The organic phase was evaporated and the residue was separated on a silica gel column (using ethyl acetate:hexane 1:3 as eluent), thereby affording Compound 5B (1.03 gram, 27% yield).

¹H NMR (300 MHz, DMSO): δ=9.45 (s, 1H), 9.27 (s, 2H), 7.10 (d, j=2.28 Hz, 2H), 7.06 (s, 4H), 6.72 (d, j=8.16 Hz, 2H), 4.25 (s, 4H), 4.23 (s, 4H) 3.24 (m, 8H), 1.19 (s, 9H), 1.18 (s, 18H)

In some embodiments, linear oligomers and cyclic compounds are prepared using the general procedures described hereinabove, while replacing the imidazolidenethione by 1,3-dihydro-2H-benzimidazole-2-thione, as exemplified hereinafter.

Synthesis of 1,3-dihydro-2H-benzimidazole-2-thione-containing Linear Oligomer and Cyclic Compounds 1,3-dihydro-2H-benzimidazole-2-thione (0.5 gram, 3.35 mmol), para-tert-butylphenol (0.75 gram, 5 mmol), paraformaldehyde (0.9 gram, 30 mmol), pTSA (0.21 gram, 1.1 mmol) and imidazolidin-2-one (0.073 gram, 0.85 mmol) were mixed in toluene (55 ml). The reaction mixture was heated to 100° C. for 13 days. After cooling to room temperature, the solvent was evaporated and a saturated sodium bicarbonate solution (50 ml) and dichloromethane (50 ml) were added. The organic phase was separated, the solvent was evaporated and the obtained residue was separated on a silica gel column (using a mixture of ethyl acetate:hexane 1:4). A mixture of linear oligomers and a mixture of cyclic products were obtained, as determined by Mass Spectroscopy. FIG. 2 presents a schematic illustration of this synthesis.

HR-MS (Compound 2C): m/z calcd for $C_{18}H_{20}N_2OS$ $[M-H]^-$ 311.1218; found 311.1188.

HR-MS (Compound 3C): m/z calcd for $C_{29}H_{34}N_2O_2S$ $[M-H]^-$ 473.2263; found 473.2228.

MS: $[M-H]^-$ =647, 971, 1295 (corresponding respectively to Cyclic Compound 4B, Cyclic Compound 6B, and Cyclic Compound 8B).

In some embodiments, a chiral cyclic structure is formed using general procedure C above, by incorporating a chiral ureatic monomer, as exemplified in the following.

Synthesis of a Chiral Derivative of Cyclic Compound 6

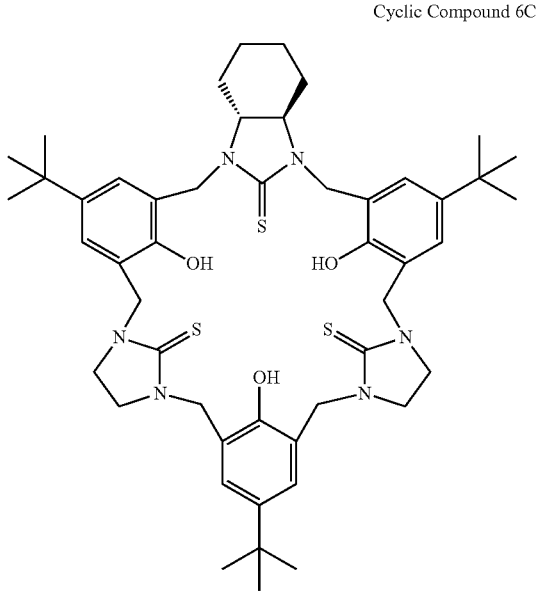 [SMILES: CC(C)(C)c1cc2c(O)c(c1)CN1CCN(Cc3cc(C(C)(C)C)cc(c3O)CN3C(=S)N(Cc4cc(C(C)(C)C)cc(c4O)CN4CCN(C2)C4=S)[C@@H]2CCCC[C@H]23)C1=S]

Cyclic Compound 6C trans-4,5-Tetramethyleneimidazolidine-2-thione (10 mg, 64 µmol), Compound 5 (45 mg, 64 µmol), paraformaldehyde (4 mg, 133 µmol) and monohydrate paratoluensulfonic acid (7 mg, 37 µmol) were heated in toluene (5 ml) at 70° C. for 3 days. The reaction mixture was cooled to room temperature and the toluene was evaporated. The crude solid residue was dissolved in dichloromethane (5 ml) and washed with a saturated aqueous solution of sodium bicarbonate (5 ml). The solvent of the organic phase was thereafter evaporated, thereby affording Cyclic Compound 6C (46.4 mg, 82% yield).

$^1$H NMR (300 MHz, CDCl$_3$): δ=8.32 (s, 2H), 7.25 (s, 3H), 7.20 (s, 2H), 7.17 (s, 1H), 4.88 (s, 2H), 4.78 (s, broad, 8H), 3.57 (s, broad, 8H), 3.43 (s, broad, 1H), 2.94 (s, 2H), 2.29 (s, 2H), 1.83 (s, 3H), 1.64 (s, 2H), 1.29 (s, 6H), 1.26 (s, 12H), 1.25 (s, 19H) ppm.

HR-MS: m/z calcd for $C_{49}H_{67}N_6O_3S_3$ $[MH]^+$ 883.4437; found 883.4465.

In some embodiments, a ureatic oligomer (or cyclic) Calixurene is formed by incorporating a ureatic monomer, as exemplified in the following:

Preparation of Hetero and Non-Symmetric Calixurenes

Using any of the general procedures described hereinabove, the modifications described hereinabove, or combinations thereof, versatile heterostructures can be obtained.

In some embodiments, the ratios of the reactants in the preparation of linear oligomers can be controlled so as to produce heterostructures.

In some embodiments, the structure of a linear oligomer and a monomer used in general procedure C hereinabove are selected so as to produce a heretostructure, as exemplified hereinafter for a urea-modified calixurene.

Synthesis of Cyclic S,S,S,O-tert-butylphenolcalixl[4,4]urene (urea-single-unit-modified Cyclic Compound 8)

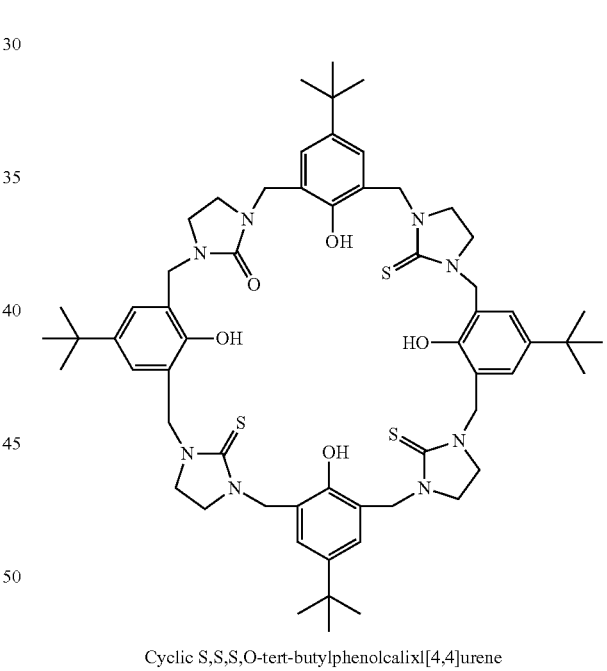

Cyclic S,S,S,O-tert-butylphenolcalixl[4,4]urene

This compound was prepared using general Procedure C described hereinabove.

3,3'-(3,3'-(2-Thioxoimidazolidine-1,3-diyl)bis(methylene)bis(5-tert-butyl-2-hydroxy-3,1-phenylene)bis(methylene))bis(1-(5-tert-butyl-2-hydroxybenzyl) imidazolidine-2-thione) (Compound 7, 0.832 gram, 0.85 mmol), paraformaldehyde (0.128 gram, 4.25 mmol), PTSA (0.081 gram, 0.42 mmol) and imidazolidin-2-one (0.073 gram, 0.85 mmol) were mixed with toluene (AR grade, 25 ml). The reaction mixture was heated to 60° C. for 48 hours, and then cooled to room temperature. The solvent was removed under reduced pressure, the crude solid residue was dissolved in hot 1M aqueous solution of NaOH (about 100 ml), and the obtained suspension was filtered to remove non-soluble impurities. The filtrate was neutralized to pH=7 by the addition of conc. HCl, resulting in precipitation of pure product as an off-white solid. The product was filtered out, washed with water and methanol and cautiously dried under vacuum, thereby affording urea-modified Cyclic Compound 8 (56% yield).

HR-MS: m/z calcd for $C_{60}H_{80}N_8O_5S_3$ [M+H]$^+$ 1089.5492; found 1089.5448

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A compound having the general Formula:

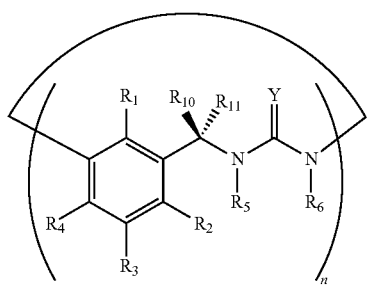

wherein:
n is an integer from 4 to 20;
$R_1$ is a reactive or functional group selected from the group consisting of hydrogen, alkyl, alkenyl, alkynyl, cycloalkyl, heteroalicyclic, aryl, heteroaryl, hydroxy, thiol, amine, amide, thioamide, carboxyl, thiocarboxyl, carbamate, thiocarbamate, sulfone, sulfoxide, sulfonamide, phosphate, phosphonate, phosphine, cyano, azide, guanyl, guanidine, azo, nitro, and hydrazine;
$R_2$-$R_4$ are each independently a reactive or functional group selected from the group consisting of hydrogen, alkyl, alkenyl, alkynyl, cycloalkyl, heteroalicyclic, aryl, heteroaryl, hydroxy, thiol, alkoxy, thioalkoxy, aryloxy, thioaryloxy, amine, amide, thioamide, carboxyl, thiocarboxyl, carbamate, thiocarbamate, sulfone, sulfoxide, sulfonamide, phosphate, phosphonate, phosphine, cyano, azide, guanyl, guanidine, azo, nitro, hydrazine, an alkylene chain of 4-30 carbon atoms, and a fatty acid moiety; any of said reactive or functional group, selected as being a chiral group and/or as comprising a radiolabeled atom; and a substance selected from the group consisting of a chemical substance, a biological substance, a pharmaceutical, a labeling moiety, a surface, and a nanoparticle,
Y is;
$R_5$ and $R_6$ are each independently selected from the group consisting of hydrogen, alkyl, cycloalkyl, heteroalicyclic, heteroaryl and aryl, or, alternatively, $R_5$ and $R_6$ form together a substituted or unsubstituted, 5-, 6- or 7-membered ring; and
$R_{10}$ and $R_{11}$ are each independently selected from the group consisting of hydrogen, alkyl, cycloalkyl, aryl, halo, hydroxy, thiol, alkoxy, thioalkoxy, aryloxy, thioaryloxy, amine, amide, thioamide, carboxyl, thiocarboxyl, carbamate, thiocarbamate, sulfone, sulfoxide, sulfonamide, phosphate, phosphonate, phosphine, cyano, azide, guanyl, guanidine, azo, nitro and hydrazine.

2. The compound of claim 1, wherein $R_1$ is selected from the group consisting of hydrogen, hydroxy and thiol.

3. The compound of claim 1, wherein at least one of said $R_1$-$R_4$ is selected from the group consisting of hydroxy and thiol.

4. A host-guest binding pair comprising a compound of claim 1 and a guest molecule associated therewithin.

5. An article comprising the compound of claim 1.

6. The article of claim 5, being selected from the group consisting of a surface having said compound applied thereon, a nanoparticle coated by said compound, a drug-delivery system comprising a bioactive agent attached to or incorporated within said compound, a chemical reagent, a biological reagent, a separation system, an edible substance, a light-sensitive substance attached to or incorporated within said compound, an oxygen-sensitive substance attached to or incorporated within said compound, a cosmetic product, an agricultural product, and a pharmaceutical product.

7. An article comprising the complex of claim 4.

8. The article of claim 7, being selected from the group consisting of a drug-delivery system comprising a bioactive agent attached to or incorporated within said compound, a chemical reagent, a biological reagent, a separation system, an edible substance, a light-sensitive substance attached to or incorporated within said compound, an oxygen-sensitive substance attached to or incorporated within said compound, a cosmetic product, an agricultural product, and a pharmaceutical product.

9. A process of preparing the compound of claim 1,

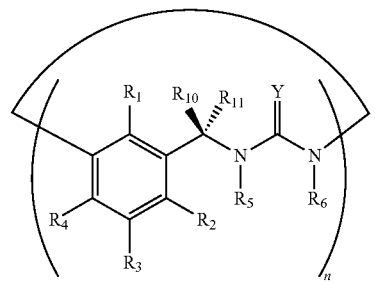

the process comprising:
reacting an aromatic moiety having the formula:

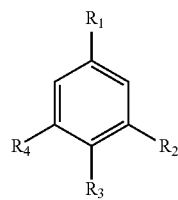

and a ureatic moiety having the formula:

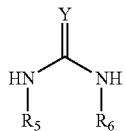

in the presence of an agent for forming a methylene bridging unit therebetween, to thereby obtain a linear oligomer having n−1 units of a formula:

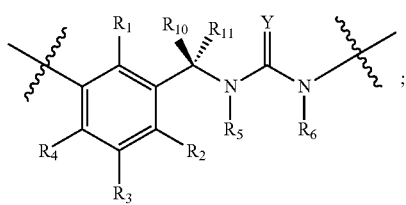

and reacting said linear oligomer having n−1 units with said aromatic moiety or said ureatic moiety, in the presence of an agent for forming a methylene bridging moiety, thereby obtaining the cyclic oligomer.

10. The process of claim 9, wherein said agent for forming said methylene bridging moiety is selected from the group consisting of an aldehyde, a ketone, an acetal, and a linear or cyclic polyoxymethylene.

* * * * *